(12) United States Patent
Fang et al.

(10) Patent No.: US 7,485,291 B2
(45) Date of Patent: Feb. 3, 2009

(54) COMPOSITIONS AND METHODS FOR GENERATING MULTIPLE POLYPEPTIDES FROM A SINGLE VECTOR USING A VIRUS DERIVED PEPTIDE CLEAVAGE SITE, AND USES THEREOF

(75) Inventors: Jianmin Fang, Foster City, CA (US); Karin Jooss, San Francisco, CA (US); Jing-Jing Qian, Foster City, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 10/452,253

(22) Filed: Jun. 3, 2003

(65) Prior Publication Data

US 2004/0265955 A1    Dec. 30, 2004

(51) Int. Cl.
| C12N 7/01 | (2006.01) |
| C12N 15/00 | (2006.01) |
| C12N 15/11 | (2006.01) |
| C12N 15/13 | (2006.01) |
| C12N 5/10 | (2006.01) |
| C12P 21/00 | (2006.01) |
| C12P 21/08 | (2006.01) |

(52) U.S. Cl. .................. 424/93.2; 435/320.1; 435/69.1; 435/325; 435/326; 536/24.1

(58) Field of Classification Search .............. 435/320.1, 435/69.1, 326; 424/93.2; 536/24.1; 530/387.1, 530/388.1
See application file for complete search history.

(56) References Cited

U.S. PATENT DOCUMENTS

| 5,436,146 | A | 7/1995 | Shenk et al. | |
| 5,643,745 | A | 7/1997 | Stuart | |
| 5,686,279 | A | 11/1997 | Finer et al. | |
| 5,753,500 | A | 5/1998 | Shenk et al. | |
| 5,846,767 | A | 12/1998 | Halpin et al. | .............. 435/69.1 |
| 5,863,765 | A | 1/1999 | Berry et al. | |
| 5,872,005 | A | 2/1999 | Wang et al. | |
| 5,994,106 | A | 11/1999 | Kovesdi et al. | |
| 6,040,183 | A | 3/2000 | Ferrari et al. | |
| 6,093,570 | A | 7/2000 | Ferrari et al. | |
| 6,127,175 | A | 10/2000 | Vigne et al. | |
| 6,133,028 | A | 10/2000 | Imler et al. | |
| 6,180,371 | B1 | 1/2001 | Lollar | |
| 6,200,560 | B1 | 3/2001 | Couto et al. | |
| 6,221,349 | B1 | 4/2001 | Couto et al. | |
| 6,251,632 | B1 | 6/2001 | Lillicrap et al. | |
| 6,271,025 | B1 | 8/2001 | Negrier et al. | |
| 6,320,029 | B1 | 11/2001 | Miekka et al. | |
| 6,331,415 | B1 | 12/2001 | Cabilly et al. | |
| 6,358,703 | B1 | 3/2002 | Cho et al. | |
| 6,376,463 | B1 | 4/2002 | Lollar | |
| 6,458,563 | B1 | 10/2002 | Lollar | |
| 6,517,830 | B1 | 2/2003 | Lollar et al. | |
| 6,518,482 | B2 | 2/2003 | Lubon et al. | |
| 6,548,286 | B1 | 4/2003 | Samulski et al. | |
| 6,599,724 | B1 | 7/2003 | Mikaelsson et al. | |
| 6,602,503 | B1 | 8/2003 | Lobb et al. | |
| 6,623,940 | B1 | 9/2003 | Ledbetter et al. | |
| 6,632,800 | B1 | 10/2003 | Russell et al. | |
| 6,642,028 | B1 | 11/2003 | Ill et al. | |
| 6,649,375 | B2 | 11/2003 | Connelly et al. | |
| 6,692,736 | B2 | 2/2004 | Yu et al. | |
| 6,852,510 | B2 | 2/2005 | Bremel et al. | |
| 6,911,200 | B2 | 6/2005 | Yu et al. | |
| 6,933,362 | B1 | 8/2005 | Belfort et al. | |
| 7,001,596 | B1 | 2/2006 | Johnson et al. | |
| 2002/0168339 | A1* | 11/2002 | Piechaczyk et al. | ........ 424/93.2 |
| 2002/0168342 | A1 | 11/2002 | Wang et al. | |
| 2003/0068307 | A1 | 4/2003 | Yu et al. | |
| 2003/0083290 | A1 | 5/2003 | Kingsman et al. | |
| 2003/0099616 | A1 | 5/2003 | Irving et al. | |
| 2003/0099932 | A1* | 5/2003 | Lorens et al. | .................. 435/5 |
| 2004/0086485 | A1 | 5/2004 | Aguilar-Cordova | |
| 2004/0131591 | A1* | 7/2004 | Kingsman et al. | .......... 424/93.2 |
| 2004/0209830 | A1* | 10/2004 | Russell et al. | .................. 514/44 |
| 2004/0235011 | A1* | 11/2004 | Cooper et al. | .................. 435/6 |
| 2004/0265955 | A1 | 12/2004 | Fang et al. | |
| 2005/0042721 | A1 | 2/2005 | Fang et al. | |
| 2005/0095705 | A1 | 5/2005 | Kadan et al. | |
| 2006/0228336 | A1 | 10/2006 | Ko | |
| 2007/0275915 | A1 | 11/2007 | Hallenbeck et al. | |

FOREIGN PATENT DOCUMENTS

EP    0623679 A1    11/1994

(Continued)

OTHER PUBLICATIONS

Burton et al, Coexpression of factor VIII heavy and light chain adeno-associated viral vectors produces biologically active protein, PNAS, Oct. 26, 1999, vol. 96, No. 22, pp. 12725-12730.*

Landry, Dr. Immunoglobulin Structure, last modified Oct. 11, 2000, downloaded Dec. 5, 2007.*

S. Furler et al., Gene Therapy 8:864-873 (2001),*Recombinant AAV vectors containing the foot and mouth disease virus 2A sequence confer efficient bicistronic gene expression in cultured cells and rat substantia nigra neurons.*

(Continued)

*Primary Examiner*—Maria B Marvich
(74) *Attorney, Agent, or Firm*—Ropes & Gray LLP; James F. Haley, Jr.; Teresa Chen

(57) ABSTRACT

Single vector constructs for expression of a functional antibody molecule are described. The vectors have a self-processing cleavage site between two heterologous DNA coding sequences allowing for expression of two coding sequences using a single promoter. Exemplary vector constructs comprise a foot and mouth disease virus (FMDV) 2A sequence. The vector constructs can be used in methods relating to antibody delivery and therapy and in the production of a biologically active antibody or fragment thereof.

20 Claims, 11 Drawing Sheets

FOREIGN PATENT DOCUMENTS

| | | |
|---|---|---|
| ES | 2 172 383 | 9/2002 |
| WO | WO 95-21249 A | 8/1995 |
| WO | WO97/49725 | 12/1997 |
| WO | WO99/46274 | 9/1999 |
| WO | WO99/46299 | 9/1999 |
| WO | WO99/61595 | 12/1999 |
| WO | WO99/61642 | 12/1999 |
| WO | WO00/23116 | 4/2000 |
| WO | WO00/71141 | 11/2000 |
| WO | WO01/03726 | 1/2001 |
| WO | WO01/27303 | 4/2001 |
| WO | WO01/45510 | 6/2001 |
| WO | WO01/68109 | 9/2001 |
| WO | WO 01-70763 A | 9/2001 |
| WO | WO02/24723 | 3/2002 |
| WO | WO02/072023 | 9/2002 |
| WO | WO03/031598 | 4/2003 |
| WO | WO03/047507 | 6/2003 |
| WO | WO03/080108 | 10/2003 |
| WO | WO03/087161 | 10/2003 |
| WO | WO03/100053 | 12/2003 |
| WO | WO2004/092348 | 10/2004 |

OTHER PUBLICATIONS

Martin Ryan et al., J. Gen. Virol. 72:2727-2732 (1991),*Cleavage of foot-and-mouth disease virus polyprotein is mediated by residues located within a 19 amino acid sequence.*

Vikram N. Vakharia et al., J. Gen. Virol. 61:3199-3207 (1987),*Proteolytic Processing of Foot-and-Mouth Disease Virus Polyproteins Expressed in a Cell-Free System from Clone-Derived Transcripts.*

Michelle L.L. Donnelly et al., J. Gen. Virol. 78:13-21 (1997),*The cleavage activities of aphthovirus and cardiovirus 2A proteins.*

Pablo de Felipe et al., Human Gene Therapy 11:1921-1931 (2000),*Tricistronic and Tetracistronic Retroviral Vectors for Gene Transfer.*

Michelle L.L. Donnelly et al., J. Gen. Virol 82:1013-1025 (2001),*Analysis of the aphthovirus 2A/2B polyprotein 'cleavage' mechanism indicates not a proteolytic reaction, but a novel translational effect: a putative ribosomal 'skip'.*

Martin D. Ryan et al., Virology 173:35-45 (1989),*Specificity of Enzyme-Substrate Interactions in Foot-and-Mouth Disease Virus Polyprotein Processing.*

Claire Halpin et al., The Plant Journal 17(4):453-459 (1999),*Self-processing 2A-polyproteins—a system for co-ordinate expression of multiple proteins in transgenic plants.*

Pablo de Felipe et al., Gene Therapy 6:198-208 (1999),*Use of the 2A sequence from foot-and-mouth disease virus in the generation of retroviral vectors for gene therapy.*

Martin D. Ryan et al.,*The EMBO Journal 13:928-933 (1994), Foot-and-mouth disease virus 2A oligopeptide mediated cleavage of an artificial polyprotein.*

Jan Roosien et al., J. Gen. Virol. 71:1703-1711 (1990),*Synthesis of foot-and-mouth disease virus capsid proteins in insect cells using baculovirus expression vectors.*

Paul J. Chaplin et al., J. Interferon and Cytokine Research 19:235-241 (1999),*Production of Interleukin-12 as a Self-Processing 2A Polypeptide.*

Pablo de Felipe, et al., "Co-translational, Intraribosomal Cleavage of Polypeptides by the Foot-and-mouth Disease Virus 2A Peptide", The Journal of Biological Chemistry, vol. 278, No. 13, pp. 11441-11448, 2003.

Pablo de Felipe, et al., "Targeting of Proteins Derived from Self-Processing Polyproteins Containing Multiple Signal Sequences", Traffic, vol. 5, pp. 616-626, 2004.

Burton et al., Coexpression of factor VIII heavy and light chain adeno-associated viral vectors produces biologically active protein, Proc. Natl. Acad. Sci. USA, Oct. 1999, vol. 96, No. 22, pp. 12725-12730.

Hosaka et al., Arg-X-Lys/Arg-Arg Motif as a Signal for Precursor Cleavage Calatyzed by Furin within the Constitutive Secretory Pathway, *J. Biol. Chem.,* Jul. 5, 1991, vol. 266, No. 19, pp. 12127-12130.

Noel et al., High In Vivo Production of a Model Monoclonal Antibody on Adenoviral Gene Transfer, *Human Gene Therapy,* Aug. 2002, vol. 13, pp. 1483-1493.

Fang, et al., 2005, "Stable Antibody Expression At Therapeutic Levels Using The 2A Peptide," Nature Biotechnology, 23(5): 584-590.

Gaken et al., 2000, "Fusagene Vectors: A Novel Strategy For The Expression of Multiple Genes From A Single Cistron," Gene Therapy 7:1979-1985.

Mah, et al., 2003, "Dual Vectors Expressing Murine Factor VIII Result In Sustained Correction Of Hemophilia A Mice," Human Gene Therapy 14:143-152.

Collet et al., A binary plasmid system for shuffling combinatorial antibody libraries, Proc. Natl. Acad. Sci. USA 89:10026-10030 (1992).

Loiler et al., Targeting recombinant adeno-associated virus vectors to enhance gene transfer to pancreatic islets and liver, Gene Therapy 10:1551-1558 (2003).

Altschul, 1997, Gapped BLAST and PSI-BLAST: a new generation of protein database search programs, Nucl Acid Res. 25(17):3389-3402.

Altshul et al., 1990, Basic local alignment search tool, J. Mol. Biol. 215:403-410.

Bernstein et al., 1997, PDGF2/c-sis mRNA leader contains a differentiation-linked internal ribosomal entry site (D-IRES, J. Biol. Chem. 272(14):9356-9362.

Borman et al., 1994, Sequences within the poliovirus internal ribosome entry segment control viral RNA synthesis, EMBO J. 13(13):3149-3157.

Brinkhous et al., 2002, Preclinical pharmacology of albumin-free B-domain deleted recombinant factor VIII, Semin Thromb Hemos 28(3):269-72 (Abstract Only).

Capecchi, 1980, High efficiency transformation by direct microinjection of DNA into cultured mammalian cells, Cell 22:479-488.

Chazenbalk et al., 1996, Evidence for negative cooperativity amoung human thyrotropin receptors overexpressed in mammalian cells, Endocrinology 137:4586-4591.

Donnelly et al., 2001, The 'cleavage' activities of foot-and-mouth disease virus 2A site-directed mutants and naturally occurring '2A-like' sequences, J. Gen. Virol. 82:1027-1041.

Donnelly et al., 2001, Analysis of the aphthovirus 2A/2B polyprotein 'cleavage' mechanism indicates not a proteolytic reaction, but a novel translational effect: a putative ribosomal 'skip', J.Gen. Virol. 82:1013-1025.

Duke et al., 1992, Sequence and structural elements that contribute to efficient encephalomyocarditis virus RNA translation, J. Virol. 66(3):1602-1609.

Dull et al., 1998, A third-generation lentivirus vector with a conditional packaging system, J. Virol. 72(11):8463-8471.

Eriksson et al., 2001, The manufacturing process for B-domain deleted recombinant factor VIII, Semin. Hematol. 38:24-31 (Abstract).

Felgner et al., 1987, Lipofection: a highly efficient, lipid-mediated DNA-transfection procedure, Proc. Natl. Acad. Sci. USA 84:7413-7417.

Frolov et al., 1998, cis-acting RNA elements required for replication of bovine viral diarrhea virus-hepatitis C virus 5' nontranslated region chimeras, RNA 4:1418-1435.

Gan et al., 1996, Internal initiation of translation directed by the 5'-untranslated region of the mRNA for eIF4G, a factor involved in the picornavirus-induced switch from cap-dependent to internal initiation, J. Biol. Chem. 271(2):623-626.

Gengrinovitch et al., 1995, Platelet factor-4 inhibits the mitogenic activity of VEGF121 and VEGF165 using several concurrent mechanisms, J. Biol. Chem. 270:15059-15065.

Ghosh et al., 2002, Baculovirus as mammalian cell expression vector for gene therapy: an emerging strategy, Mol. Ther. 6(1):5-11.

Glass et al., 1993, Identification of the hepatitis A virus internal ribosome entry site: in vivo and in vitro analysis of bicistronic RNAs containing the HAV 5' noncoding region, Virology 193:842-852.

Green et al., 1994, Antigen-specific human monoclonal antibodies from mice engineered with human lg heavy and light chain YACs, Nat. Genetics 7(1):13-21.

Green, 1999, Antibody engineering via genetic engineering of the mouse: XenoMouse strains are a vehicle for the facile generation of therapeutic human monoclonal antibodies, J. Immunol. Meth. 231:11-23.

Guo et al., 1996, Evaluation of promoter strength for hepatic gene expression in vivo following adenovirus-mediated gene transfer, Gene Ther. 3:802-810.

Gura, 2002, Therapeutic antibodies: magic bullets hit the target, Nature 417:584-586.

Hagedorn, 2002, Domain swapping in a COOH-terminal fragment of platelet factor 4 generates potent angiogensis inhibitors, Cancer Res. 62:6884-6890.

Hamstra and Rehemtulla, 1999, Toward an enzyme/prodrug strategy for cancer gene therapy: endogenous activation of carboxypeptidase A mutants by the PACE/Furin family of propeptidases, Hum. Gene Ther. 10:235-248.

Hartley et al., 1976, Naturally occurring murine leukemia viruses in wild mice: characterization of a new "amphotropic" class, J. Virol. 19(1):19-25.

High, 2003, Gene transfer as an approach to treating hemophilia, Semin. Thromb. Hemost. 29(1):107-20.

Hitt et al., 2000, Adenovirus vectors for human gene therapy, Adv. Virus Res. 55:479-505.

Holash et al., 2002, VEGF-Trap: a VEGF blocker with potent antitumor effects, Proc. Natl. Acad. Sci. USA 99(17):11393-98.

Houdebine, 2002, Antibody manufacture in transgenic animals and comparisons with other systems, Opin. Biotech. 13:625-629.

Huez et al., 1998, Two independent internal ribosome entry sites are involved in translation initiation of vascular endothelial growth factor mRNA, Mol. Cell Biol. 18(11):6178-6190.

Ikonomou et al., 2003, Insect cell culture for industrial production of recombinant proteins, Appl. Microbiol. Bitoech. 62(1):1-20.

III et al., 1997, Optimization of the human factor VIII complentary DNA expression plasmid for gene therapy of hemophilia A, Blood Coag. Fib. 8(2):S23-S30.

Jackson et al., 1990, The novel mechanism of initiation of picornavirus RNA translation, Trends Biochem. Sci. 15(12):477-83.

Jackson et al., 1995, Internal initiation of translation in eukaryotes: the picornavirus paradigm and beyond, RNA 1(10):985-1000.

Jakobovits et al., 1995, Production of fully human antibodies by transgenic mice, Curr. Opin. in Bio. 6(5):561-566.

Jakobovits et al., 1998, Production and selection of antigen-specific fully human monoclonal antibodies from mice engineered with human lg loci, Adv. Drug Deliv. Rev. 31:33-42.

Jang et al., 1990, Cap-independent translation of encephalomyocarditis virus RNA: structural elements of the internal ribosomal entry site and involvement of cellular 57-kD RNA-binding protein, Genes & Dev. 4:1560-1572.

Kim et al., 1990, Use of the human elongation factor 1 alpha promoter as a versatile and efficient expression system, Gene 91:217-23.

Kjalke et al., 1995, Amino acid residues 721-729 are required for full factor VIII activity, Eur. J. Biochem. 234(3):773-779.

Klein et al., 1987, High-velocity microprojectiles for delivering nucleic acids into living cells, Nature 327:70-73.

Knott et al., 2002, Tetracycline-dependent gene regulation: combinations of transregulators yield a variety of expression windows, Biotechniques 32(4):796-800.

Kohler et al., 1976, Derivation of specific antibody-producing tissue culture and tumor lines by cell fusion, Eur. J. Immunol. 6:511-519.

Kolber et al., 1995, Inhibition of development of murine melanoma lung metastases by systemic administration of recombinant platelet factor 4, J. Natl. Cancer Instit.87:304-309.

Kotin, 1994, Prospects for the use of adeno-associated virus as a vector for human gene therapy, Hum. Gene Ther. 5:793-801.

Lamikarna et al., 2005, In vivo evaluation of an EIAV vector for the systemic genetic delivery of therapeutic antibodies, Gene Therapy-12:988-998.

Lenting et al., 1998, The life cycle of coagulation factor VIII in view of its structure and function, Blood 92(11):3983-3996.

Lind et al., 1995, Novel forms of B-domain-deleted recombinant factor VIII molecules. Construction and biochemical characterization, Eur. J. Biochem. 232:19-27.

Little et al., 2000, Of mice and men: hybridoma and recombinant antibodies, Immunol. Today 21(8):364-70.

Liu et al., 1999, Hydrodynamics-based transfection in animals by systemic administration of plasmid DNA, Gene Ther. 6:1258-1266.

Lopez-Lastra et al., 1997, Characterization of an internal ribosomal entry segment within the 5' leader of avian reticuloendotheliosis virus type A RNA and development of novel MLV-REV-based retroviral vectors, Hum. Gene Ther. 8:1855-1865.

Macejak et al., 1991, Internal initiation of translation mediated by the 5' leader of a cellular mRNA, Leishmania RNA virus 1-mediated cap-independent translation, Nature 353:90-94.

Maga et al., 1995, Leishmania RNA virus 1-mediated cap-independent translation, Mol. Cell. Biol. 15(9):4884-4889.

Maione et al., 1990, Inibition of angiogenesis by recombinant human platelet factor-4 and related peptides, Science 247:77-79.

Mannino et al., 1988, Liposome mediated gene transfer, BioTechn. 6(7):682-690.

McCormick et al., 2003, Individualized human scFv vaccines produces in plants: humoral anti-idiotype responses in vaccinated mice confirm relevance to the tumor lg, J. Immunol. Meth. 278:95-104.

Mendez et al., 1997, Functional transplant of megabase human immunoglobulin loci recapitulates human antibody response in mice, Nat. Gen. 15:146-156.

Miller, 1992, Human gene therapy comes of age, Nature 357:455-460.

Mulligan et al., 1980, Expression of a bacterial gene in mammalian cells, Science 209:1422-1427.

Nakai et al., 1998, Adeno-associated viral vector-mediated gene transfer of human blood coagulation factor IX into mouse liver, Blood 91(12):4600-4607.

Needleman et al., 1970, A general method applicable to the search for similarities in the amino acid sequence of two proteins, J. Mol. Biol. 48:443-453.

Niwa et al., 1991, Efficient selection for high-expression transfectants with a novel eukaryotic vector, Gene 108(2):193-199.

No et al., 1996, Ecdysone-inducible gene expression in mammalian cells and transgenic mice, Proc. Natl. Acad. Sci. USA 93:3346-3351.

O'Rourke et al., 2002, Comparison of gene transfer efficiencies and gene expression levels achieved with equine infectious anemia virus- and human immunodeficiency virus type 1-derived lentivirus vectors, J. Virol. 76(3):1510-1515.

Oh et al., 1992, Homeotic gene Antennapedia mRNA contains 5'-noncoding sequences that confer translational initiation by internal ribosome binding, Gene & Dev. 6:1643-1653.

Ory et al., 1996, A stable human-derived packaging cell line for production of high titer retrovirus/vesicular stomatitis virus G pseudotypes, Proc. Natl. Acad. Sci. USA 93:11400-11406.

Osterberg et al., 2001, B-domain deleted recombinant factor VIII formulation and stability, Semin Hematol. 38(2 Suppl 4):40-3.

Osterwalder et al., 2001, A conditional tissue-specific transgene expression system using inducible GAL4, Proc. Natl. Acad. Sci. USA 98(22):12596-601.

Palmenberg, 1990, Proteolytic processing of picornaviral polyprotein, Ann. Rev. Microbiol. 44:603-623.

Paulus, 1998, Protein splicing: A novel form of gene expression and paradigm for self-catalyzed protein rearrangements, Pure & Appl. Chem. 70(1):1-8.

Pearson et al., 1988, Improved tools for biological sequence comparison, Proc. Natl. Acad. Sci. USA, 85:2444-2448.

Perollet, 1998, Platelet factor 4 modulates fibroblast growth factor 2 (FGF-2) activity and inhibits FGF-2 dimerization, Blood 91:3289-32-99.

Pittman et al., 1993, Biochemical, immunological and in vivo functional characterization of B-domain-deleted factor VIII, Blood 81:2925-2935.

Pogue et al., 2002, Making an ally from an enemy: plant virology and the new agriculture, Ann .Rev. Phytopathol. 40:45-74.

Pollack et al., 1999, Transgenic milk as a method for the production of recombinant antibodies, J. Immunol. Meth. 231:147-157.

Rivera et al., 1996, A humanized system for pharmacologic control of gene expression, Nature Med. 2(9):1028-1032.

Sandberg et al., 2001, Structural and functional characterization of B-domain deleted recombinant factor VIII, Semin. Hematol. 38(2 Suppl 4):4-12.

Schillberg et al., 2003, Molecular farming of recombinant antibodies in plants, Cell Mol. Life Sci. 60(3):433-35.

Sharpe et al., 1990, Growth inhibition of murine melanoma and human colon carcinoma by recombinant human platelet factor 4, J. Natl. Cancer Inst. 82:848-853.

Shigekawa et al., 1988, Electroporation of eukaryotes and prokaryotes: a general approach to the introduction of macromolecules into cells, BioTechn. 6(8):742-751.

Smith et al., 1981, Comparison of biosequences, Adv. Appl. Math. 2:482-489.

Southern et al., 1982, Transformation of mammalian cells to antibiotic resistance with a bacterial gene under control of the SV40 early region promoter, J. Mol. Appl. Genet. 1(4):327-341.

Stein et al., 1998, Translation of vascular endothelial growth factor mRNA by internal ribosome entry: implications for translation under hypoxia, Mol. Cell. Biol. 18(6):3112-3119.

Streatfield et al., 2003, Plant-based vaccines, Int. J. Parasitol. 33:479-93.

Sugden et al., 1985, A vector that replicates as a plasmid and can be efficiently selected in B-lymphoblasts transformed by Epstein-Barr virus, Mol. Cell Biol. 5(2):410-413.

Suhr et al., 1998, High level transactivation by a modified Bombyx ecdysone receptor in mammalian cells without exogenous retinoid X receptor, Proc. Natl. Acad. Sci. USA 95:7999.

Takahashi et al., 1993, A mutation of furin causes the lack of precursor-processing activity in human colon carcinoma LoVo cells, Biochem. Biophys. Res. Comm. 195:1019-26.

Tanaka et al., 1997, Viral vector-mediated transduction of a modified platelet factor 4 cDNA inhibits angiogenesis and tumor growth, Nat. Med. 3(4):437-442.

Teerink et al., 1995, The human insulin-like growth factor II leader 1 contains an internal ribosomal entry site, Biochim Biophys. Acta 1264:403-408.

Thompson, 2003, Structure and function of the factor VIII gene and protein, Semin. Thromb. Hemost. 29(1):11-22.

Torrent et al., 1996, Stable MLV-VL30 dicistronic retroviral vectors with a VL30 or MoMLV sequence promoting both packaging of genomic RNA and expression of the 3' cistron, Hum. Gene Ther. 7:603-612.

Tsukiyama-Kohara et al, 1992, Internal ribosome entry site within hepatitis C virus RNA, J. Virol. 66(3):1476-1483.

Vagner et al., 1995, Alternative translation of human fibroblast growth factor 2 mRNA occurs by internal entry of ribosomes, Mol. Cell Biol. 15(1):35-44.

Van der Velden et al., 1999, The role of the 5' untranslated region of an mRNA in translation regulation during development, Int. J. Biochem & Cell Bio. 31:87.

Vandendriessche et al., 2003, Gene therapy for the hemophilias, J. Thromb. Haemost. 1:1550.

Witte et al., 1998, Monoclonal antibodies targeting the VEGF receptor-2 (Flk1/KDR) as an anti-angiogenic therapeutic strategy, Cancer Metastasis 17:155-161.

Xu et al., 2001, Optimization of transcriptional regulatory elements for constructing plasmid vectors, Gene 272:149.

Ye et al., 1999, Regulated delivery of therapeutic proteins after in vivo somatic cell gene transfer, Science 283:88.

Yonemura et al., 1993, Efficient production of recombinant human factor VIII by co-expression of the heavy and light chains, Protein Eng. 6:669-674.

Young et al., 1998, Production of recombinant antibodies in the milk of transgenic animals, Res. Immunol. 149(6):609-610.

Zhang et al., 1999, High levels of foreign gene expression in hepatocytes after tail vein inejections of naked plasmid DNA, Human Gene Ther. 10:1735-1737.

Zufferey et al., 1997, Multiply attenuated lentiviral vector achieves efficient gene delivery in vivo, Nat. Biotech. 15:871-875.

Zufferey et al., 1998, Self-inactivating lentivirus vector for safe and efficient in vivo gene delivery, J. Virol. 72(12):9873-9880.

Li et al., A hepatocellular carcinoma-specific adenovirus variant, CV890, eliminates distant human liver tumors in combination with doxorubicin, Cancer Res. 61:6428-6436 (2001).

* cited by examiner ual., EMBO J. 13:928-933 (1994)); and insect cells (Roosien et al., J. Gen. Virol. 71:1703-1711 (1990)). The FMDV 2A-mediated cleavage of a heterologous polyprotein for a biologically relevant molecule has been shown for IL-12 (p40/p35 heterodimer; Chaplin et al., J. Interferon Cytokine Res. 19:235-241 (1999). In transfected COS-7 cells, FMDV 2A mediated the cleavage of a p40-2A-p35 polyprotein into biologically functional subunits p40 and p35 having activities associated with IL-12.

COMPOSITIONS AND METHODS FOR GENERATING MULTIPLE POLYPEPTIDES FROM A SINGLE VECTOR USING A VIRUS DERIVED PEPTIDE CLEAVAGE SITE, AND USES THEREOF

FIELD OF THE INVENTION

The invention relates to novel vector constructs designed to express self-processing recombinant polypeptides, preferably, full length immunoglobulins or fragments thereof. The vectors may be used for in vitro, ex vivo or in vivo delivery of foreign, therapeutic transgenes to somatic cells, or in the production of recombinant polypeptides by vector-transfected somatic cells.

BACKGROUND OF THE INVENTION

To express two or more proteins from a single viral or non-viral vector, multiple promoters or an internal ribosome entry site (IRES) sequence are commonly used to drive the individual genes. The use of two promoters within a single vector can result in promoter interference resulting in inefficient expression of both genes. If two genes are linked via an IRES sequence the expression level of the second gene may be significantly reduced (Furler et al., Gene Therapy 8:864-873 (2001)).

The linking of proteins in the form of polyproteins in a single open reading frame is a strategy adopted in the replication of many viruses including picornaviridae. Upon translation, virus-encoded proteinases mediate rapid intramolecular (cis) cleavages of a polyprotein to yield discrete mature protein products. Foot and Mouth Disease viruses (FMDV) are a group within the picornaviridae which express a single, long open reading frame encoding a polyprotein of approximately 225 kD. The full length translation product undergoes rapid intramolecular (cis) cleavage at the C-terminus of a 2A region occurring between the capsid protein precursor (P1-2A) and replicative domains of the polyprotein 2BC and P3, and this cleavage is mediated by proteinase-like activity of the 2A region itself (Ryan et al., J. Gen. Virol. 72:2727-2732 (1991); Vakharia et al., J. Virol. 61:3199-3207 (1987)). Ryan designed constructs identifying the essential amino acid residues for expression of the cleavage activity by the FMDV 2A region. 2A domains have also been characterized from aphthoviridea and cardioviridae of the picornavirus family (Donnelly et al., J. Gen. Virol. 78:13-21 (1997).

The mechanism of action for 2A may involve ribosomal skipping between codons which prevents formation of peptide bonds (de Felipe et al., Human Gene Therapy 11:1921-1931 (2000); Donnelly et al., J. Gen. Virol. 82:1013-1025 (2001); although it has been considered that the domain acts more like an autolytic enzyme (Ryan et al., Virol. 173:35-45 (1989)). Nevertheless, the utility of a 2A domain single gene vector construct for expression of full length polypeptides including antibodies or heterodimeric proteins can be fully appreciated from the embodiments described hereinafter.

Studies in which the FMDV 2A coding region was cloned into expression vectors and transfected into target cells have established that FMDV 2A cleavage of artificial reporter polyproteins is efficient in a broad range of heterologous expression systems (wheat-germ lysate and transgenic tobacco plant (Halpin et al., U.S. Pat. No. 5,846,767 (1998) and Halpin et al., The Plant Journal 17:453-459 (1999)); Hs 683 human glioma cell line (de Felipe et al., Gene Therapy 6:198-208 (1999); hereinafter referred to as "de Felipe II"); rabbit reticulocyte lysate and human HTK-143 cells (Ryan et In a recent report, the FMDV 2A sequence was incorporated into retroviral vectors, alone or combined with different IRES sequences to construct bicistronic, tricistronic and tetracistronic retroviral vectors. These vectors were shown to express drug resistance and reporter genes in producer cell lines and infected cultured fibroblasts. To test the efficiency of 2A-mediated gene expression in animals and the potential for the vector constructs for in vivo gene therapy, Furler (2001) generated recombinant adeno-associated viral (AAV) genomes encoding α-synuclein and EGFP or Cu/Zn superoxide dismutase (SOD-1) and EGFP linked via the FMDV 2A sequence. EGFP and α-synuclein were expressed at substantially higher levels from 2A vectors than from corresponding IRES-based vectors, while SOD-1 was expressed at comparable or slightly higher levels. Furler also demonstrated that the 2A sequence results in bicistronic gene expression in vivo after injection of 2A-dependent AAVs into rat substantia nigra.

Previous attempts to express a full length antibody/immunoglobulin molecule using a single vector have met with limited success, typically resulting in unequal levels of expression of the heavy and light chains of the antibody/immunoglobulin molecule, and more particularly, a lower level of expression for the second gene. In order to express a fully biological functional antibody from a single vector, equimolar expression of the heavy and light chains is required. Additionally, conventional vectors relying on dual promoter regulation of gene expression are invariably affected by promoter interaction (ie, promoter interference) which may compromise equimolar expression of the genes. Other factors that limit the ability to express two or more coding sequences from a single vector include the packaging limitation of the vector itself. For example, in considering the appropriate vector/coding sequence, factors to be considered include: the capacity of the vector (e.g., approx. 4,500 bp for AAV); the duration of expression of the recombinant molecule by a vector-transfected cell (e.g., short term expression for adenoviral vectors); the cell types infected by the vector if a viral vector is used; and the desired expression level of the target gene product(s). The requirement for controlled expression of two or more gene products together with the packaging limitations of viral vectors such as adenovirus and AAV, limits the choices with respect to vector construction and systems for expression of immunoglobulins or fragments thereof.

Accordingly, there remains a need for improved gene expression systems in the context of expression of immunoglobulins or fragments thereof which correct for the deficiencies inherent in currently available technology (e.g., the use of an IRES). The present invention addresses this need.

SUMMARY OF THE INVENTION

The present invention provides a system for expression of full length antibody molecules or fragments thereof based on essentially equal expression of heavy and light chain coding sequences under transcriptional control of the same promoter wherein translation is mediated by self-processing cleavage site, e.g., a 2A or 2A-like sequence. Accordingly, the invention provides an improved vector system containing the coding sequence for an antibody heavy chain, a 2A sequence and the coding sequence for an antibody light chain wherein the 2A sequence provides the opportunity to engineer either whole protein antibody molecules or fragments thereof such that they are cleaved apart co-translationally with high efficiency.

In one aspect, the invention provides a vector for expression of a full length immunoglobulin chain or a fragment thereof, comprising in the 5' to 3' direction, a promoter operably linked to the coding sequence for the heavy chain of an antibody molecule or a fragment thereof, a sequence encoding a self-processing cleavage site and the coding sequence for the light chain of an antibody molecule or a fragment thereof, wherein the sequence encoding the self-processing cleavage site is inserted between the heavy chain coding sequence and the light chain coding sequence.

In a related aspect, the invention provides a vector for expression of a full length immunoglobulin chain or a fragment thereof, comprising in the 5' to 3' direction, a promoter operably linked to the coding sequence for the light chain of an antibody molecule or a fragment thereof, a sequence encoding a self-processing cleavage site and the coding sequence for the heavy chain of an antibody molecule or a fragment thereof, wherein the sequence encoding the self-processing cleavage site is inserted between the light chain coding sequence and the heavy chain coding sequence.

Preferred self-processing cleavage sites include a 2A sequence, e.g., a 2A sequence cleavage site from Foot and Mouth Disease Virus (FMDV).

The vector may be any recombinant vector capable of expression of the full length antibody molecule or fragment thereof, for example, an adeno-associated virus (AAV) vector, a lentivirus vector, a retrovirus vector, a replication competent adenovirus vector, a replication deficient adenovirus vector and a gutless adenovirus vector, a nonviral plasmid, and a herpes virus vector. The vector will typically comprise a promoter selected from the group consisting of an elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP) a cytomegalovirus enhancer/chicken beta-actin promoter (CAG), a tetracycline responsive promoter (TRE), a transthyretin promoter (TTR), a simian virus 40 promoter (SV40) and a CK6 promoter.

The vector may further comprise a signal sequence for the heavy and/or light chain antibody coding sequences.

In a preferred aspect of the invention, the heavy and light chain antibody coding sequences are expressed in an equimolar ratio.

The invention further provides a host cell transduced with a vector comprising a self-processing cleavage site and use of such cells in generating a recombinant antibody or fragment thereof.

Other and further objects, features and advantages are apparent from the following description of the embodiments for the invention given the purpose of disclosure when taken in conjunction with the accompanying drawings.

DETAILED DESCRIPTION OF THE INVENTION

Figure 1:
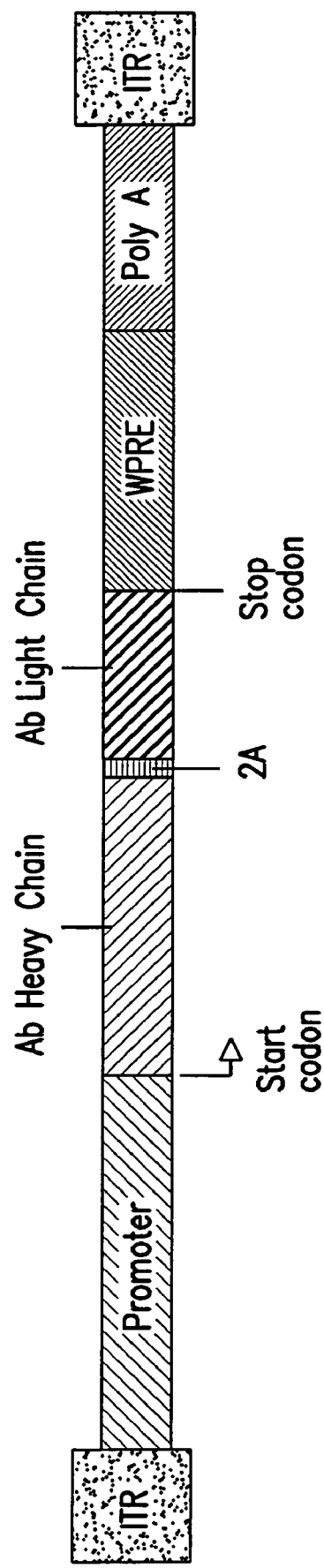
FIG. 1 depicts an AAV expression cassette encoding the heavy and light chain for an antibody as described in Example 1.
Figure 2:
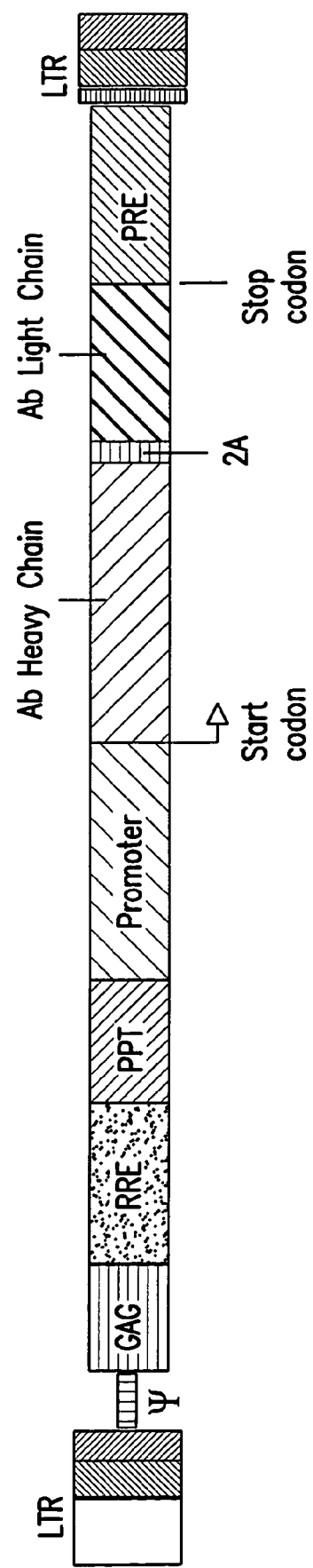
FIG. 2 depicts a lenti virus expression cassette encoding the heavy and light chain for an antibody.
Figure 3:
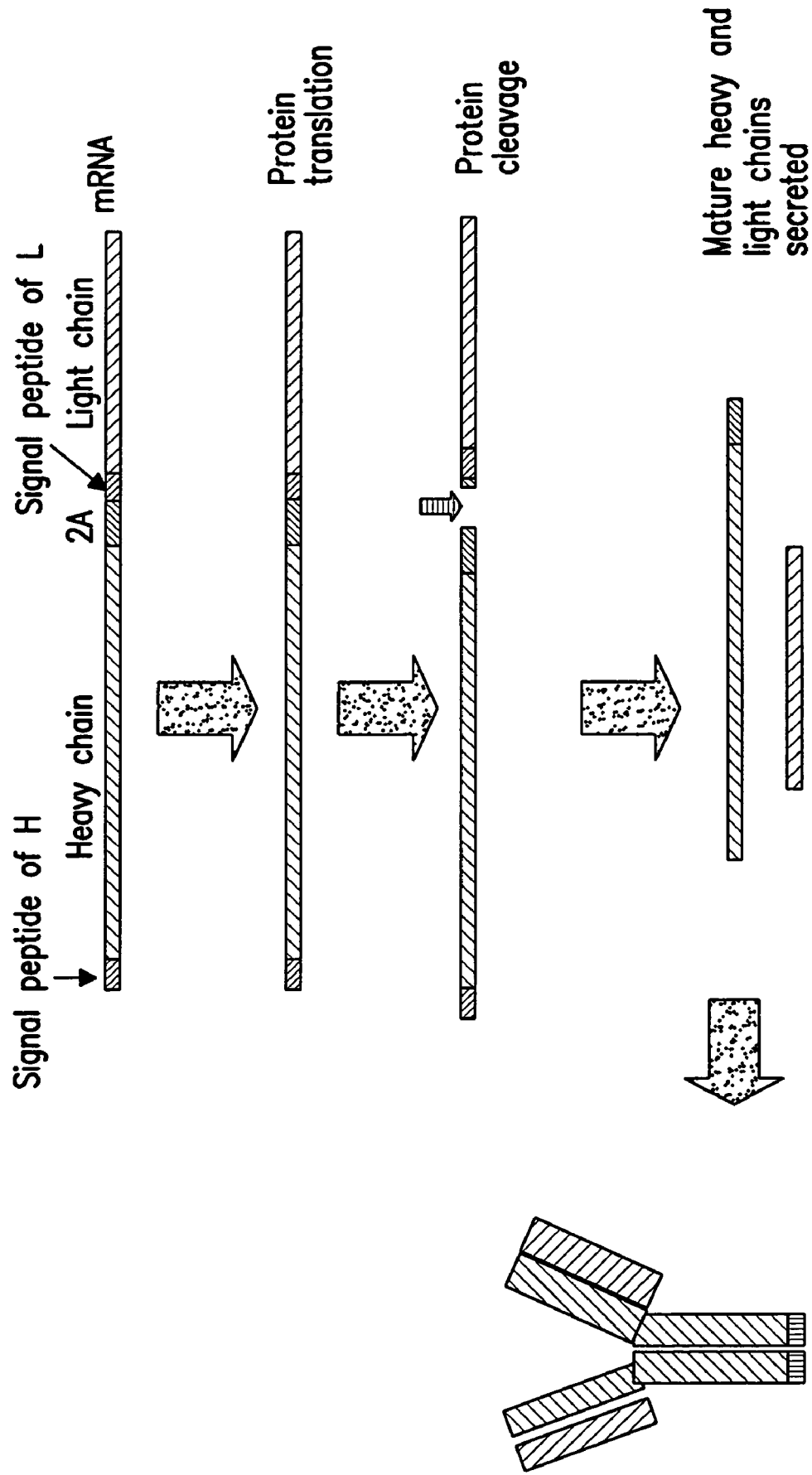
FIG. 3 is a schematic illustration of the bioprocessing of a polyprotein for an anti-FLK-1 whole IgG with an AAV H2AL construct.

Antibodies are proteins that are hererodimers of a heavy and light chain and have proven extremely difficult to express as full length proteins from a single vector in mammalian culture expression systems. An ideal viral or nonviral single gene vector would permit the delivery and expression of two or more antibodies with bi- or multiple-specificities (e.g., quadromas/bispecific antibodies). The antibodies can be engineered antibodies including but not limited to single chain antibodies, full-length antibodies or antibody fragments.

The present invention provides vector constructs comprising a promoter operably linked to a first protein coding sequence, a self-processing coding sequence and a second coding sequence for one additional protein, wherein the self-processing coding sequence is inserted between the first protein coding sequence and the second protein coding sequence. The inclusion of such cleavage or self-processing sequences in the vector construct enables the expression from a single promoter of multiple proteins/peptides linked as a polyprotein, in host cells or organisms. The cleavage or self-processing sequences also facilitate the generation of individual proteins/peptides from the polyprotein during or after the translation process. These individual proteins/peptides can then assemble into, for example, an antibody/immunoglobulin, a heterodimeric protein or a soluble receptor or fragments thereof.

Definitions

The term "vector", as used herein, refers to a DNA or RNA molecule such as a plasmid, virus or other vehicle, which contains one or more heterologous or recombinant DNA sequences and is designed for transfer between different host cells. The terms "expression vector" and "gene therapy vector" refer to a vector that has the ability to incorporate and express heterologous DNA fragments in a foreign cell. A cloning or expression vector may comprise additional elements, for example, the expression vector may have two replication systems, thus allowing it to be maintained in two organisms, for example in human cells for expression and in a prokaryotic host for cloning and amplification. A "vector" refers to a nucleic acid sequence encoding one or more proteins under the control of a functional promoter and possibly also an enhancer. Any suitable vector can be employed that is appropriate for introduction of nucleic acids into eukaryotic cells, more particularly animal cells, such as mammalian, e.g., human cells is useful in practicing the invention.

The term "replication defective" as used herein relative to a viral gene therapy vector of the invention means the viral vector cannot further replicate and package its genomes. For example, when a cell of a subject is infected with rAAV virions, the heterologous gene is expressed in the infected cells, however, due to the fact that the infected cells lack AAV rep and cap genes and adenovirus accessory function genes, the rAAV is not able to replicate.

As used herein, a "retroviral transfer vector" refers to the expression vector that comprises a nucleotide sequence that encodes a transgene and that further comprises nucleotide sequences necessary for packaging of the vector. Preferably, the retroviral transfer vector also comprises the necessary sequences for expressing the transgene in cells.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and that further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "pseudotyped" refers to the replacement of a native envelope protein with a heterologous or functionally modified envelope protein.

The term "operably linked" as used herein relative to a recombinant DNA construct or vector means nucleotide components of the recombinant DNA construct or vector are directly linked to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

A "promoter" is a DNA sequence that directs the binding of RNA polymerase and thereby promotes RNA synthesis.

"Enhancers" are cis-acting elements that stimulate or inhibit transcription of adjacent genes. An enhancer that inhibits transcription also is termed a "silencer". Enhancers can function (i.e. be operably linked to a coding sequence) in either orientation, over distances of up to several kilobase pairs (kb) from the coding sequence and from a position downstream of a transcribed region.

The terms "transcriptional regulatory protein", "transcriptional regulatory factor" and "transcription factor" are used interchangeably herein, and refer to a cytoplasmic or nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to the DNA response element.

As used herein, the terms "stably transformed", "stably transfected" and "transgenic" refer to cells that have a non-native (heterologous) nucleic acid sequence integrated into the genome. Stable transfection is demonstrated by the establishment of cell lines or clones comprised of a population of daughter cells containing the transfected DNA. In some cases, "transfection" is not stable, i.e., it is transient. In the case of transient transfection, the exogenous or heterologous DNA is expressed, however, the introduced sequence is not integrated into the genome. It is episomal.

As used herein, the terms "biological activity" and "biologically active", refer to the activity attributed to a particular protein in a cell line in culture or in cell-free system, such as ligand-receptor assay in ELISA plates. It will be appreciated that the "biological activity" of such a protein may vary somewhat dependent upon culture or assay conditions and is generally reported as a range of activity. Accordingly, a "biologically inactive" protein generated from 2A cleavage refers to the protein that retains similar activity of the protein as it is found in nature.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

The term "administering", as used herein refers to delivering a vector to a cell. Such administering may take place in vivo, in vitro or ex vivo. In ex vivo administration, primary cells are taken from a subject, a vector is administered to the cells to produce transduced cells and the transduced cells are readministered to the same or a different subject.

A "self-processing cleavage site" is defined herein as a post-translational or co-translational processing cleavage site, such as a 2A site or domain or a 2A-like site or domain.

The term "host cell", as used herein refers to cells which are transduced, transformed or transfected with a vector. The vector may be, for example, in the form of a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transfected cell and progeny thereof.

2A and 2A-Like Sequences

A "self-processing cleavage site" is defined herein as a post-translational or co-translational processing cleavage site or a 2A site or domain. A 2A site or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site or domain demonstrates "auto-proteolysis" or "cleavage" by cleaving its own C-terminus in cis to produce primary cleavage products (Furler; Palmenberg, Ann. Rev. Microbiol. 44:603-623 (1990)).

For the present invention, the DNA sequence encoding the self-processing cleavage site is derived from a virus, preferably a picornavirus including but not limited to the entero-, rhino-, cardio-, aphtho- and Foot-and-Mouth Disease (FMDV) viruses, and most preferably, from FMDV. Self-processing cleavage sites include but are not limited to 2A and 2A-like domains (Donnelly et al., J. Gen. Virol. 82:1027-1041 (2001), expressly incorporated by reference in its entirety.

Positional subcloning of a 2A sequence between two heterologous DNA sequences for the inventive vector construct allows the delivery of two genes through a single expression vector. More preferably, FMDV 2A sequences provide a unique means to express and deliver from a single viral vector, two or multiple proteins/peptides which can be individual parts of, for example, an antibody, heterodimeric receptors or heterodimeric proteins.

FMDV 2A is a polyprotein region which functions in the FMDV genome to direct a single cleavage at its own C-terminus, thus functioning only in cis. The FMDV 2A domain is nineteen amino acids in length (NFDLLKLAGDV ESNPGPFF (SEQ ID NO: 1); Ryan et al., J. Gen. Virol. 72:2727-2732 (1991)) and oligopeptides of as few as fourteen amino acid residues are able to mediate cleavage at the 2A C-terminus in a fashion similar to its role in the native FMDV polyprotein processing.

Variations of the 2A sequence have been studied for their ability to mediate efficient processing of polyproteins (Donnelly MLL et al. 2001). Homologues and variants of a 2A sequence are included within the scope of the invention and include but are not limited to the sequences presented in Table 1, below:

or to FMDV, thus 2A activity does not discriminate between heterologous proteins and an FMDV-derived polyprotein in its ability to function or mediate cleavage.

The small size of the 2A coding sequence further enables its use in vectors with a limited packing capacity for a transgene such as AAV. The utility of AAV vectors can be further expanded since the 2A sequence eliminates the need for dual promoters. The expression levels of individual proteins/peptides from a promoter driving a single open reading frame comprising the first gene, the 2A sequence, and the second gene are more equimolar compared to those vector systems using IRES sequences or a dual promoter. Elimination of dual promoters reduces promoter interference that may result in reduced and/or impaired levels of expression for either gene.

In one preferred embodiment, the FMDV 2A sequence for the vector according to the invention encodes amino acid residues comprising NFDLLKLAGDVESNPGPFF (SEQ ID NO:1). Alternatively, the vector according to the invention may encode amino acid residues for other 2A-like regions as discussed in Donnelly et al., J. Gen. Virol. 82:1027-1041 (2001) and including but not limited to a 2A-like domain from picornavirus, insect virus, Type C rotavirus, trypansome repeated sequences and the bacterium, *Thermatoga maritima*.

A nucleic acid sequence variant that encodes a 2A or 2A-like polypeptide, includes a nucleic acid coding sequence for a 2A or 2A-like polypeptide which has a different codon for one or more of the amino acids relative to that of the parent nucleotide. Such variants are specifically contemplated and encompassed by the present invention. Sequence variants of 2A polypeptides described herein are included within the scope of the invention as well.

As used herein, the term "sequence identity" means nucleic acid or amino acid sequence identity in two or more aligned sequences, aligned using a sequence alignment program. The term "% homology" is used interchangeably herein with the term "% identity" herein and refers to the level of nucleic acid or amino acid sequence identity between two or more aligned sequences, when aligned using a sequence alignment pro-

TABLE 1

Table of Exemplary 2A Sequences

| Sequence | ID |
|---|---|
| NFDLLKLAGDVESNPGPFF | (SEQ ID NO:1) |
| LLKLAGDVESNPGP | (SEQ ID NO:2) |
| NFDLLKLAGDVESNPGP | (SEQ ID NO:3) |
| QLLNFDLLKLAGDVESNPGP | (SEQ ID NO:4) |
| APVKQTLNFDLLKLAGDVESNPGP | (SEQ ID NO:5) |
| VTELLYRMKRAETYCPRPLLAIHPTEARHKQKIVAPVKQTLNFDLLKLA GDVESNPGP | (SEQ ID NO:6) |
| LLAIHPTEARHKQKIVAPVKQTLNFDLLKLAGDVESNPGP | (SEQ ID NO:7) |
| EARHKQKIVAPVKQTLNFDLLKLAGDVESNPGP | (SEQ ID NO:8) |

Distinct advantages of 2A sequences and variants thereof their use in subcloning into vectors for in order to obtain a self-processing polyprotein. Any proteins/peptides comprising a self-processing polyprotein obtained through the constructs of the invention are expressed in equimolar or close to equimolar amounts following the apparently autolytic cleavage of the polyprotein by the FMDV 2A domain. These proteins may be heterologous to the vector itself, to each other gram. For example, as used herein, 80% homology means the same thing as 80% sequence identity determined by a defined algorithm, and accordingly a homologue of a given sequence has greater than 80% sequence identity over a length of the given sequence.

Exemplary computer programs that can be used to determine identity between two sequences include, but are not limited to, the suite of BLAST programs, e.g., BLASTN, BLASTX, TBLASTX, BLASTP and TBLASTN, all of which are publicly available on the Internet. See, also, Altschul, S. F. et al., 1990 and Altschul, S. F. et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In accordance with the present invention, also encompassed are sequence variants of 2A polypeptides that have 80, 85, 88, 89, 90, 91, 92, 93, 94, 95, 96, 97, 98, 99% or more sequence identity to the native sequence for a 2A polypeptide described herein.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. 2A sequence variants that encode a polypeptide with the same biological activity as the 2A polypeptides described herein and hybridize under moderate to high stringency hybridization conditions are considered to be within the scope of the present invention.

As a result of the degeneracy of the genetic code, a number of coding sequences can be produced which encode the same 2A or 2A-like polypeptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

Antibody Production

As used herein, a "first protein coding sequence" refers to a nucleic acid sequence encoding a protein molecule including, but not limited to a chain for an immunoglobulin or a fragment thereof, a cytokine or a fragment thereof, a growth factor or a fragment thereof, a soluble or membrane-associated receptor or a fragment thereof, a viral protein or a fragment thereof, an immunogenic protein or a fragment thereof, a transcriptional regulator or a fragment thereof, a proapoptotic molecule or a fragment thereof, a tumor suppressor or a fragment thereof, an angiogenesis inhibitor or fragment thereof, etc.

As used herein, a "second protein coding sequence" refers to a nucleic acid sequence encoding a protein molecule including a chain for an antibody/immunoglobulin or a fragment thereof, a cytokine or a fragment thereof, a growth factor or a fragment thereof, a soluble or membrane-associated receptor or a fragment thereof, a viral protein or a fragment thereof, an immunogenic protein or a fragment thereof, a transcriptional regulator or a fragment thereof, a proapoptotic molecule or a fragment thereof, a tumor suppressor or a fragment thereof, an angiogenesis inhibitor or fragment thereof, etc.

The sequence encoding the chain for an antibody/immunoglobulin or a fragment thereof includes a heavy chain or a fragment thereof for an IgG, IgM, IgD, IgE or IgA. The sequence encoding the chain for an antibody/immunoglobulin or a fragment thereof also includes the light chain or a fragment thereof for an IgG, IgM, IgD, IgE or IgA. Genes for whole antibody molecules as well as modified or derived forms thereof, include fragments like Fab, single chain Fv(scFv) and F(ab')$_2$. The antibodies and fragments can be animal-derived, human-mouse chimeric, humanized, DeImmunized™ or fully human. The antibodies can be bispecific and include but are not limited to a diabody, quadroma, miniantibody, ScBs antibody and knobs-into-holes antibody.

The production and recovery of the antibodies themselves can be achieved in various ways as known in the art (Harlow et al., "Antibodies, A Laboratory Manual", Cold Spring Harbor Lab, (1988)).

For example, the production of the antibody or analogue can be undertaken by culturing the modified recombinant host cell under culture conditions appropriate for the growth of the host cells and the expression of the coding sequences. In order to monitor the success of expression, the antibody levels with respect to the antigen are monitored using standard techniques such as ELISA, RIA and the like.

The antibodies are then recovered from the culture using standard techniques known in the art. Purified forms of these antibodies can, of course, be readily prepared by standard purification techniques, preferably including affinity chromatography via protein A, protein G or protein L columns, or with respect to the particular antigen, or even with respect to the particular epitope of the antigen for which specificity is desired. Antibody can also be purified with conventional chromatography, such as an ion exchange or size exclusion column, in conjunction with other technologies, such as ammonia sulfate precipitation and size-limited membrane filtration. The expression systems are preferably designed to include signal peptides so that the resulting antibodies are secreted into the medium; however, intracellular production is also possible.

Particularly in the case of therapeutic agents or diagnostic agents for use in vivo, it is highly advantageous to employ antibodies and their analogues with fully human characteristics. These reagents avoid the undesired immune responses engendered by antibodies or analogues which have characteristics marking them as originating from non-human species. To address possible host immune responses to amino acid residues derived from 2A peptides in an antibody product, a proteolytic cleavage site may be inserted (using standard methodology known in the art) between the first protein and the 2A sequence so as to remove the 2A sequence from the antibody.

The proteolytic cleavage sites which can be inserted between the first protein and the 2A sequence may include, but are not limited to:

a). Factor Xa cleavage site: IE(D)GR (SEQ ID NO:9)
b). Thrombin cleavage site: LVPRGS (SEQ ID NO:10)
c). Signal peptidase I cleavage site: e.g. LAGFATVAQA (SEQ ID NO:11)
d). Furin cleavage site: RXK(R)R (SEQ ID NO:12)

Other Heterologous Proteins

The vector constructs of the invention may comprise a transgene such as a therapeutic gene that will ameliorate hereditary or acquired diseases when expressed in a targeted cell by using gene transfer technology methods well known in the art. In one particular aspect, the therapeutic gene is the normal DNA sequence corresponding to a defective gene, for example, the normal DNA sequence for LDL receptors and α-antitrypsin. In another aspect, the transgene may encode, for example, an Ig, a cytokine gene or soluble receptor gene, or a combination thereof.

If an Ig gene is selected, the expression of the gene in a targeted cell may provide a treatment to malignancies by stimulating immune responses which result in suppression of tumor growth and/or killing of tumor cells. If a soluble receptor gene is chosen, the gene when expressed by a target cell will enable the chelation or sequestration of an undesired cognate ligand suppressing a cellular immune response and/or tumor growth.

Exemplary transgene sequences encoding a heterodimeric protein include but are not limited to nucleotide sequences encoding proteins for HIF-1α and HIFβ (HIF), p35 and p40 (IL-12), chain A and chain B of insulin, integrins such as but not limited to alpha V beta 3 or alpha V beta 5, and the light chain and the heavy chain of Factor VIII.

Exemplary transgene sequences encoding a soluble receptor include but are not limited to the TNF p55 and p75 receptor, IL-2 receptor, FGF receptors, VEGF receptors, TIE2, IL-6 receptor and IL-1 receptor.

Exemplary transgene sequences encoding a cytokine include, but are not limited to: IL-1, IL-2, IL-3, IL-4, IL-5, IL-6, 11-7, IL-8, IL-9, IL-10, IL-11, IL-12, IL-13, IL-18, INF-α, -β, and -γ, GM-CSF, G-CSF, erythropoietin.

Exemplary transgene sequences encoding growth factors include but are not limited to: VEGF, FGF, Angiopoietin-1 and 2, PDGF, EGF, IGF, NGF, IDF, HGF, TGF-α, TGF-beta.

Exemplary transgene sequences encoding pro-apoptotic factors include but are not limited to: Bad, Bak, Bax, Bcl2, Bcl-Xs, Bik, Caspases, FasL, and TRAIL.

Exemplary transgene sequences encoding tumor suppressor proteins or cell cycle regulators include but are not limited to: p53, p16, p19, -21, p27, PTEN, RB1.

Exemplary transgene sequences encoding angiogenesis regulators include but are not limited to: angiostatin, endostatin, TIMPs, antithrombin, PF4, PEDF, PEX, troponin I, thrombospondin, tumstatin, 16 Kd Prolactin.

Cloned sequences and full length nucleotides encoding any of the above-referenced biologically active molecules may be obtained by well known methods in the art (Sambrook et al., 1989). In general, the nucleic acid sequences may be obtained from public databases and/or scientific publications.

Homologues and variants of antibody and other heterologous protein coding sequences are included within the scope of the invention based on "sequence identity" or "% homology" to known nucleic acid sequences which are available in publicly available databases and/or selective hybridization under stringent conditions, as described above for 2A sequences. Homologues and variants of antibody and other heterologous protein amino acid sequences are further included within the scope of the invention. Such sequences may be identified based on "sequence identity" to known sequences using publicly available databases and sequence alignment programs as set forth above.

Vectors for Use in Practicing the Invention

The present invention contemplates the use of any of a variety of vectors for introduction of a gene encoding a therapeutic protein into mammalian cells. Such vectors may be viral or of non-viral origin. Non-viral gene delivery methods which may be employed in the practice of the invention include but are not limited to plasmids, liposomes, nucleic acid/liposome complexes, cationic lipids and the like.

Viruses can efficiently transduce cells and introduce their own DNA into a host cell. In generating recombinant viral vectors, non-essential genes are replaced with a gene encoding a therapeutic protein. Exemplary vectors include but are not limited to, viral and non-viral vectors, such as retroviruses (including lentiviruses), an adenovirus (Ad) including replication competent, replication deficient and gutless forms thereof, an adeno-associated virus (AAV), a simian virus 40 (SV-40), a bovine papilloma virus, an Epstein-Barr virus, a herpes virus, a vaccinia virus, a Moloney murine leukemia virus, a Harvey murine sarcoma virus, a murine mammary tumor virus, a Rous sarcoma virus and a nonviral plasmid.

More preferably, the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern et al., J., J Mol Appl Genet. 1982; 1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) or G418.

Reference to a vector or other DNA sequences as "recombinant" merely acknowledges the operable linkage of DNA sequences which are not typically operably linked as isolated from or found in nature. Regulatory (expression/control) sequences are operatively linked to a nucleic acid coding sequence when the expression/control sequences regulate the transcription and, as appropriate, translation of the nucleic acid sequence. Thus expression/control sequences can include promoters, enhancers, transcription terminators, a start codon (i.e., ATG) in front of the coding sequence, splicing signal for introns and stop codons.

Adenovirus gene therapy vectors are known to exhibit strong transient expression, excellent titer, and the ability to transduce dividing and non-dividing cells in vivo (Hitt et al., Adv in Virus Res 55:479-505 (2000)). The recombinant Ad vectors of the instant invention comprise: (1) a packaging site enabling the vector to be incorporated into replication-defective Ad virions; and (2) a therapeutic compound coding sequence. Other elements necessary or helpful for incorporation into infectious virions, include the 5' and 3' Ad ITRs, the E2 and E3 genes, etc.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005, incorporated herein by reference in its entirety. A therapeutic compound-encoding gene is commonly inserted into adenovirus in the deleted E1A, E1B or E3 region of the virus genome. Preferred adenoviral vectors for use in practicing the invention do not express one or more wild-type Ad gene products, e.g., E1a, E1b, E2, E3, and E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175, expressly incorporated by reference herein in their entirety. Adenovirus vectors are purified and formulated using standard techniques known in the art.

Recombinant AAV vectors are also characterized in that they are capable of directing the expression and the production of the selected transgenic products in targeted cells. Thus, the recombinant vectors comprise at least all of the sequences of AAV essential for encapsidation and the physical structures for infection of the recombinant AAV (rAAV) virions for use in practicing the present invention may be produced using standard methodology, known to those of skill in the art and are constructed such that they include, as operatively linked components in the direction of transcription, control sequences including transcriptional initiation and termination sequences, and the coding sequence for a therapeutic compound or biologically active fragment thereof. These components are bounded one the 5' and 3' end by functional AAV ITR sequences. By "functional AAV ITR sequences" is meant that the ITR sequences function as intended for the rescue, replication and packaging of the AAV virion. Hence, AAV ITRs for use in the vectors of the invention need not have a wild-type nucleotide sequence, and may be altered by the insertion, deletion or substitution of nucleotides or the AAV ITRs may be derived from any of several AAV serotypes. An AAV vector is a vector derived from an adeno-associated virus serotype, including without limitation, AAV-1, AAV-2, AAV-3, AAV-4, AAV-5, AAV-6, AAV-7, etc. Preferred AAV vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large Rep proteins (Rep78 and Rep68), typically by mutating the start codon following p5 from ATG to ACG, as described in U.S. Pat. No. 6,548,286, expressly incorporated by reference herein. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety and include those techniques within the knowledge of those of skill in the art.

In practicing the invention, host cells for producing rAAV virions include mammalian cells, insect cells, microorganisms and yeast. Host cells can also be packaging cells in which the AAV rep and cap genes are stably maintained in the host cell. Host cells can be producer cells in which the AAV vector genome is stably maintained and packaged. Exemplary packaging and producer cells are derived from 293, A549 or HeLa cells. AAV vectors are purified and formulated using standard techniques known in the art.

Retroviral vectors are a common tool for gene delivery (Miller, 1992, Nature 357: 455-460). Retroviral vectors and more particularly lentiviral vectors may be used in practicing the present invention. Retroviral vectors have been tested and found to be suitable delivery vehicles for the stable introduction of a variety of genes of interest into the genomic DNA of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding a transgene to a specific type of target cells is highly desirable for gene therapy applications.

The present invention provides retroviral vectors which include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentivirus include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771, including Table 1, incorporated herein by reference).

The present invention provides retroviral packaging systems for generating producer cells and producer cell lines that produce retroviruses, and methods of making such packaging systems. Accordingly, present invention also provides producer cells and cell lines generated by introducing a retroviral transfer vector into such packaging systems (e.g., by transfection or infection), and methods of making such packaging cells and cell lines.

The packaging systems of the present invention comprise at least two packaging vectors: a first packaging vector which comprises a first nucleotide sequence comprising a gag, a pol, or gag and pot genes; and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of retroviral systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pot and env.

Lentiviruses share several structural virion proteins in common, including the envelope glycoproteins SU (gp120) and TM (gp41), which are encoded by the env gene; CA (p24), MA (p17) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880

Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

Optionally, a conditional packaging system is used, such as that described by Dull et al., 1998, J. Virology 72(11):8463-8471. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

The gene therapy vectors of the invention typically include heterologous control sequences, which include, but are not limited to, constitutive promoters, such as the cytomegalovirus (CMV) immediate early promoter, the RSV LTR, the MoMLV LTR, and the PGK promoter; tissue or cell type specific promoters including mTTR, TK, HBV, hAAT, regulatable promotes, enhancers, etc. Preferred promoters include the LSP promoter (Ill et al., Blood Coagul. Fibrinolysis 8S2: 23-30 (1997)), the EF1-alpha promoter (Kim et al., Gene 91(2):217-23 (1990)) and Guo et al., Gene Ther. 3(9):802-10 (1996)). A most preferred promoter is elongation factor 1-alpha promoter (EF1a), phosphoglycerate kinase-1 promoter (PGK), cytomegalovirus immediate early gene promoter (CMV), chimeric liver-specific promoters (LSP), cytomegalovirus enhancer/chicken beta-actin promoter (CAG), tetracycline responsive promoter (TRE), transthyretin promoter (TTR), simian virus 40 promoter (SV40) and CK6 promoter.

The present invention contemplates the inclusion of a gene regulation system for the controlled expression of an anti-angiogenic compound or factor. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent to the gene to be regulated.

Exemplary gene regulation systems that may be employed in practicing the present invention include, the Drosophila ecdysone system (Yao et al., Proc. Nat. Acad. Sci., 93:3346 (1996)), the Bombyx ecdysone system (Suhr et al., Proc. Nat. Acad. Sci., 95:7999 (1998)), the Valentis GeneSwitch® synthetic progesterone receptor system which employs RU-486 as the inducer (Osterwalder et al., Proc Natl Acad Sci 98(22): 12596-601 (2001)); the Tet™ & RevTet™ Systems (BD Biosciences Clontech), which employs small molecules, such as tetracycline (Tc) or analogues, e.g. doxycycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerization and a system based on heterodimerization (Rivera et al., Nature Med, 2(9): 1028-1032 (1996); Ye et al., Science 283: 88-91 (2000)).

Preferred gene regulation systems for use in practicing the present invention are the ARIAD Regulation Technology and the Tet™ & RevTet™ Systems.

Delivery of Nucleic Acid Constructs Encoding Antibody and Other Heterologous Protein Sequences to Cells The vector constructs of the invention comprising nucleic acid sequences encoding antibodies or fragments thereof or other heterologous proteins in the form of self-processing recombinant polypeptides may be introduced into cells in vitro, ex vivo or in vivo for delivery of foreign, therapeutic or transgenes to somatic cells, or in the production of recombinant polypeptides by vector-transfected somatic cells.

The vector constructs of the invention may be introduced into cells in vitro or ex vivo using standard methodology known in the art. Such techniques include transfection using calcium phosphate, micro-injection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. USA 84:7413-7417 (1987)), and nucleic acid delivery using high-velocity microprojectiles (Klein et al., Nature 327:70-73 (1987)).

The vectors may be administered in vivo via various routes (e.g., intradermally, intravenously, into the brain, intraportally, intraperitoneally, intramuscularly, into the bladder etc), to deliver two or more proteins connected via a 2A sequence to expression of the two or more proteins in animal models or human patients. Dependent upon the route of administration, the therapeutic proteins elicit their effect locally (in brain or bladder) or systemically (other routes of administration). The use of tissue specific promoters 5' to the open reading frame results in tissue specific expression of the proteins encoded by the entire open reading frame.

Various methods that introduce a recombinant vector carrying a transgene into target cells in vitro, ex vivo or in vivo have been previously described and are well known in the art. The present invention provides for therapeutic methods, vaccines, and cancer therapies by infecting targeted cells with the recombinant vectors containing a transgene of interest, and expressing the transgene in the targeted cell.

For example, in vivo delivery of recombinant vector constructs vector constructs of the invention may be targeted to a wide variety of organ types including brain, liver, blood vessels, muscle, heart, lung and skin.

In the case of ex vivo gene transfer, the target cells are removed from the host and genetically modified in the laboratory using a vector construct of the present invention and methods well known in the art.

The recombinant vector constructs of the invention can be administered using conventional modes of administration including but not limited to the modes described above. The recombinant vector constructs of the invention may be in a variety of dosages which include but are not limited to liquid solutions and suspensions, microvesicles, liposomes and injectable or infusible solutions. The preferred forms depend upon the mode of administration and the therapeutic application.

The many advantages to be realized in using the inventive recombinant vector constructs of the invention in antibody gene therapy include administration of a single vector for long-term and sustained antibody expression in patients; in vivo expression of an antibody or fragment thereof having full biological activities; and the natural posttranslational modifications of the antibody generated in human cells.

The recombinant vector constructs of the present invention find further utility in the in vitro production of recombinant antibodies for use in therapy. Methods for recombinant protein production are well known in the art and may be utilized for expression of recombinant antibodies using the recombinant vector constructs described herein.

The invention further provides a method for producing a recombinant immunoglobulin or a fragment thereof, by introducing an expression vector into a cell to obtain a transfected cell, wherein the vector comprises a promoter operably linked to a coding sequence for an immunoglobulin heavy chain or a fragment thereof, a 2A or 2A-like sequence and a coding sequence for an immunoglobulin light chain or a fragment thereof, and wherein the 2A or 2A-like sequence is inserted between the coding sequence for the immunoglobulin heavy chain or a fragment thereof and the coding sequence for the light chain or the fragment thereof. It will be appreciated that the either the coding sequence for the immunoglobulin heavy chain or the coding sequence for the immunoglobulin light chain may be 5' to the 2A sequence (i.e. first) in a given vector construct.

In one exemplary aspect of the invention, this is followed by one or more of the following steps:

(1) culturing the transfected cell under conditions for selecting a cell expressing the immunoglobulin or the fragment thereof;

(2) measuring expression of the immunoglobulin or the fragment thereof; and (3) obtaining the immunoglobulin or the fragment thereof.

Another aspect of the invention provides a cell for expressing a recombinant immunoglobulin or a fragment thereof, wherein the cell comprises an expression vector for the expression of two or more immunoglobulin chains or fragments thereof, a promoter operably linked to a first coding sequence for an immunoglobulin chain or a fragment thereof, a 2A or 2A-like sequence and a second coding sequence for an immunoglobulin chain or a fragment thereof, wherein the 2A or 2A-like sequence is inserted between the first and the second coding sequence.

In a related aspect, the invention provides a method for delivery of recombinant immunoglobulins or proteins to naive or tumor bearing mice, i.e. viral or non-viral vectors, by injecting mice (e.g., intraperitoneally, intramuscularly, into the brain, intravenously or into the portal vein) with a recombinant viral or non-viral vector wherein the vector comprises a promoter operably linked to a first coding sequence for an immunoglobulin chain or a fragment thereof, a 2A or 2A-like sequence and a second coding sequence for an immunoglobulin chain or a fragment thereof, and wherein the 2A or 2A-like sequence is inserted between the coding sequence for the immunoglobulin heavy chain or a fragment thereof and the coding sequence for the light chain or the fragment thereof.

In one exemplary aspect of the invention, this is followed by one or more of the following steps:

(1) collecting serum samples from transduced mice;

(2) measuring expression of the recombinant immunoglobulins, fragments thereof or recombinant proteins; and (3) determining the therapeutic or biological effect of the recombinant protein(s) or immunoglobulin(s) expressed locally or systemically by the vectors in relevant animal models.

The objects of the invention have been achieved by a series of experiments, some of which are described by way of the following non-limiting examples.

The practice of the present invention will employ, unless otherwise indicated, conventional techniques of molecular biology, microbiology, cell biology, biochemistry and immunology, which are within the knowledge of those of skill of the art. Such techniques are explained fully in the literature, such as, "Molecular Cloning: A Laboratory Manual", second edition (Sambrook et al., 1989); "Current Protocols in Molecular Biology" (F. M. Ausubel et al., eds., 1987); "Animal Cell Culture" (R. I. Freshney, ed., 1987), each of which is hereby expressly incorporated herein by reference.

EXAMPLE 1

Construction of AAV 2A Expression Construct.

An AAV vector encoding full length heavy and light chains of a rat anti-FLK-1 monoclonal antibody and a 2A sequence was constructed. The variable and constant regions of the antibody heavy and light chains were cloned from a cDNA of the parental hydridoma cells using the Polymerase Chain Reaction (PCR). The cDNA was synthesized with reverse transcriptase from total RNA isolated from the hydridoma cells using Qiagen's total RNA purification kit. The nucleotide sequence of the monoclonal antibody was analyzed using an automatic sequencing system (Applied Biosciences) and consensus sequences were obtained from the sequencing data derived from multiple independent PCR reactions.

The DNA fragments that encode the rat antibody heavy chain, 2A sequence and antibody light chain were linked together by PCR extension. Artificial FMDV 2A oligo nucleotides were synthesized based on the 2A peptide sequence APVKQTLNFDLLKLAGDVESNPGP (SEQUENCE ID NO:5). The heavy and light chain fragments were amplified from the cloned plasmids that encode the full-length antibody heavy and light chains respectively. During the PCR, a Hind III restriction endonucleotidase site was added to the 5' prime end of the heavy chain and a Not I site to the 3' prime end of the light chain. The fused heavy chain—2A—light chain DNA fragment was digested with Hind III and Not I, which was purified from agarose gel. The purified DNA fragment was inserted into the AAV backbone flanked with Hind III and Not I by using T4 DNA ligase. The AAV construct contains an EF1-alpha promoter driving expression of the monoclonal antibody heavy chain—2A sequence—light chain. In variant forms, a native signal peptide (leader) is included in the heavy or light chain, respectively, to facilitate secretion of the polypeptides upon synthesis. In addition, the construct contains a WPRE and poly A sequence to ensure high level gene expression (FIG. 1).

EXAMPLE 2

Expression of a Rat IGG from an AAV H2AL Construct by 293T Cells

Figure 4:
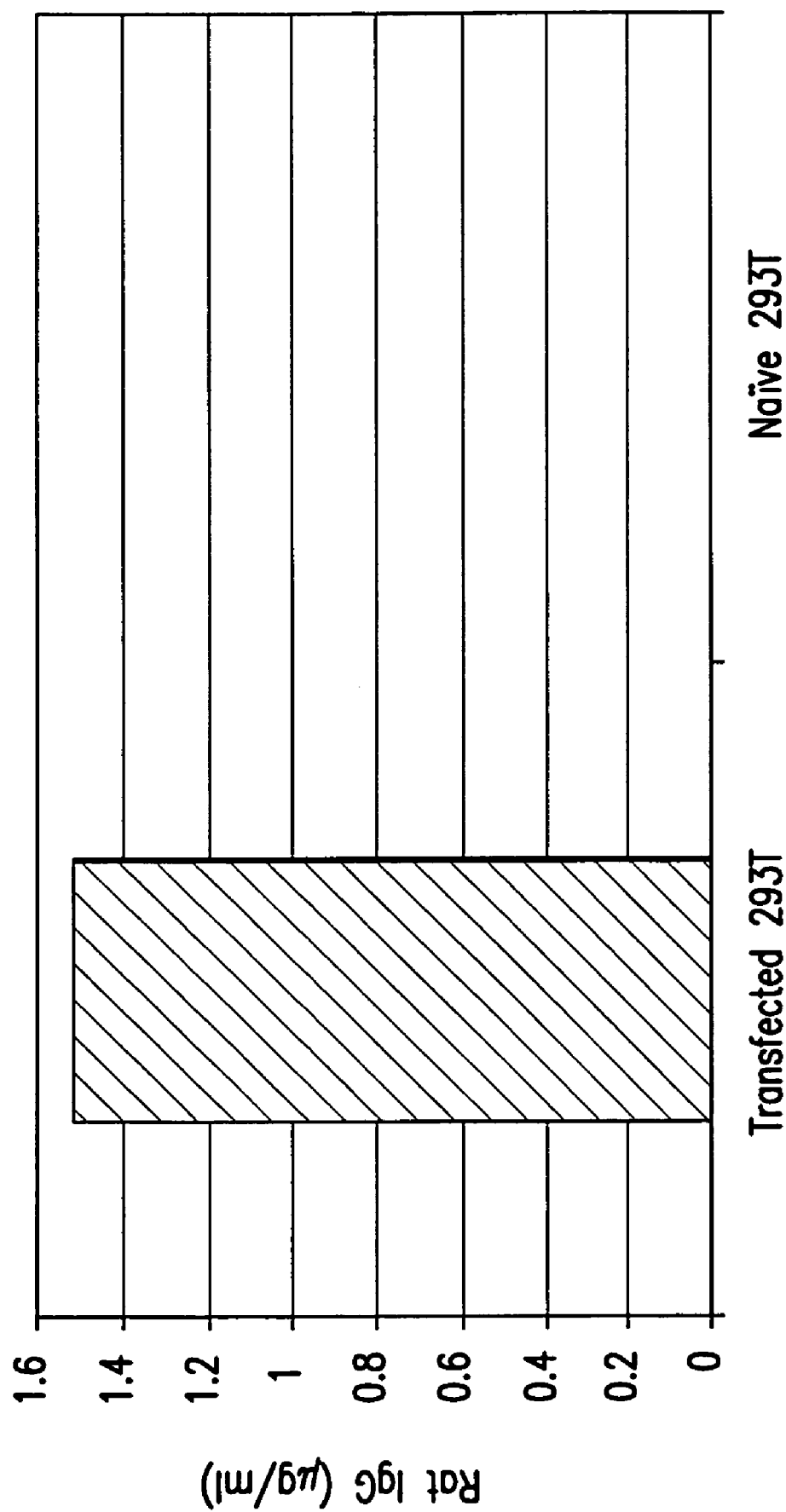
FIG. 4 demonstrates the expression of rat anti-FLK-1 IgG in the supernatant of 293T cells transfected with anti-FLK-1 Ig/AAV H2AL construct.

An AAV vector construct (AAV H2AL) encoding the heavy and light chain of a monoclonal IgG antibody against murine FLK-1 and linked by insertion of the FMDV 2A sequence, was transiently transfected into 60% confluent 293T cells. Cells were grown in Iscove's Modified Dulbecco's Medium (IMDM) supplemented with 10% fetal bovine serum, 1% L-glutamine, and 1% penicillin-streptomycin solution (Invitrogen). Transfection was carried out using a Fugene 6 transfection kit (Roche), containing a lipids-based transfection reagent resulting in uptake of foreign DNA into mammalian cells. AAV H2AL plasmid DNA was mixed with the transfection reagent according to the manufacturer's instruction and the DNA-lipid mixture was added to the cell culture medium. The transfected cells were incubated for 48 or 72 hours and the supernatants analyzed for antibody expression. The mAb concentration was determined using a rat IgG ELISA assay (Bethyl Laboratories), in which mAb IgG protein was captured by an immobilized anti-rat IgG antibody on ELISA plates and detected by an anti-rat IgG Fc antibody conjugated with HRP. The ELISA plates were developed and mAb concentrations were calculated based on OD reading of the samples based on a standard curve with known rat IgG concentrations. ELISA assay results revealed that the recombinant rat IgG antibody was expressed at high levels in the supernatant of 293T cells transfected with the AAV plasmid containing a 2A sequence (FIG. 4).

The biological activity of the antibody was evaluated for neutralizing activity in a VEGF-FLK-1 binding assay. In this assay, recombinant VEGF (vascular endothelial cell growth factor, from R & D Systems) was coated on ELISA plates (Nunc), then blocked with 5% milk. The rat anti-FLK-1 antibody was pre-incubated at various concentrations with recombinant FLK-1-Fc (R & D Systems). The antibody/FLK-1 mixture was transferred to ELISA wells and the plates were incubated to allow VEGF-FLK-1 binding. After rinsing with balance solution, a goat anti-FLK-1 antibody conjugated with biotin was used to detect bound FLK-1, which was visualized by streptavidin-HRP (PharMingen) after color development with the HRP substrate.

Figure 5:
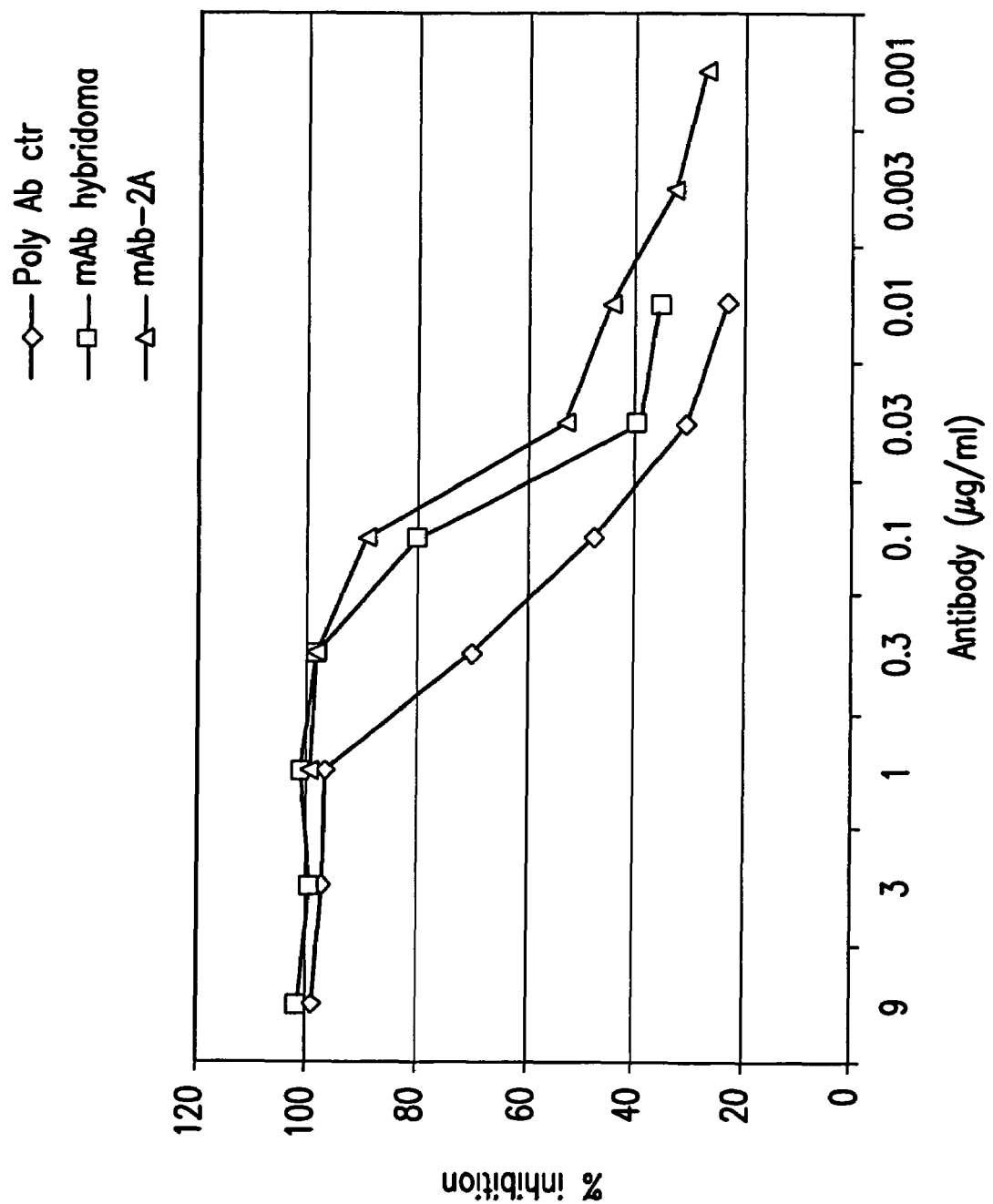
FIG. 5 demonstrates the biological activity of anti-FLK-1 IgG in the supernatant of 293 T cells transfected with the anti-FLK-1 IgG/AAV H2AL construct.

By using the VEGF/FLK-1 (ligand-receptor) binding assay, it was demonstrated that the antibody expressed from 293T cells following transient transfection exhibits full biological activity, similar to that of the native antibody expressed by parent hybridoma cells (FIG. 5).

The antibody expressed utilizing the 2A sequence was further characterized using Western blot analysis. Protein in the supernatant of transiently transfected 293T cells (transfected with AAV H2AL plasmid) or from that of hybridoma cells was separated by polyacrylamide gel electrophoresis under reducing or non-reducing conditions. For the reducing gel, protein samples were mixed with 2×LDS sample buffer (Invitrogen), boiled, loaded on pre-cast 12% Tris-Glycine gel (Invitrogen), and run with Tris-Glycine SDS running buffer. For the non-reducing gel, protein samples were mixed with 2× native TrisGly sample buffer (Invitrogen), loaded on pre-cast 12% Tris-Glycine gel (Invitrogen), and run with Tris-Glycine native running buffer (Invitrogen). After electrophoresis, the proteins were transferred to nitrocellulose membranes in Tris-Glycine transfer buffer with 20% methanol. The membranes were blocked with blocking solution and stained with HRP-conjugated anti-rat IgG. The membrane blots were treated with SuperSignal West Pico Chemiliminescent substrate kit (Pierce) and protein bands were visualized in Biome film (Kodak).

Figure 6:
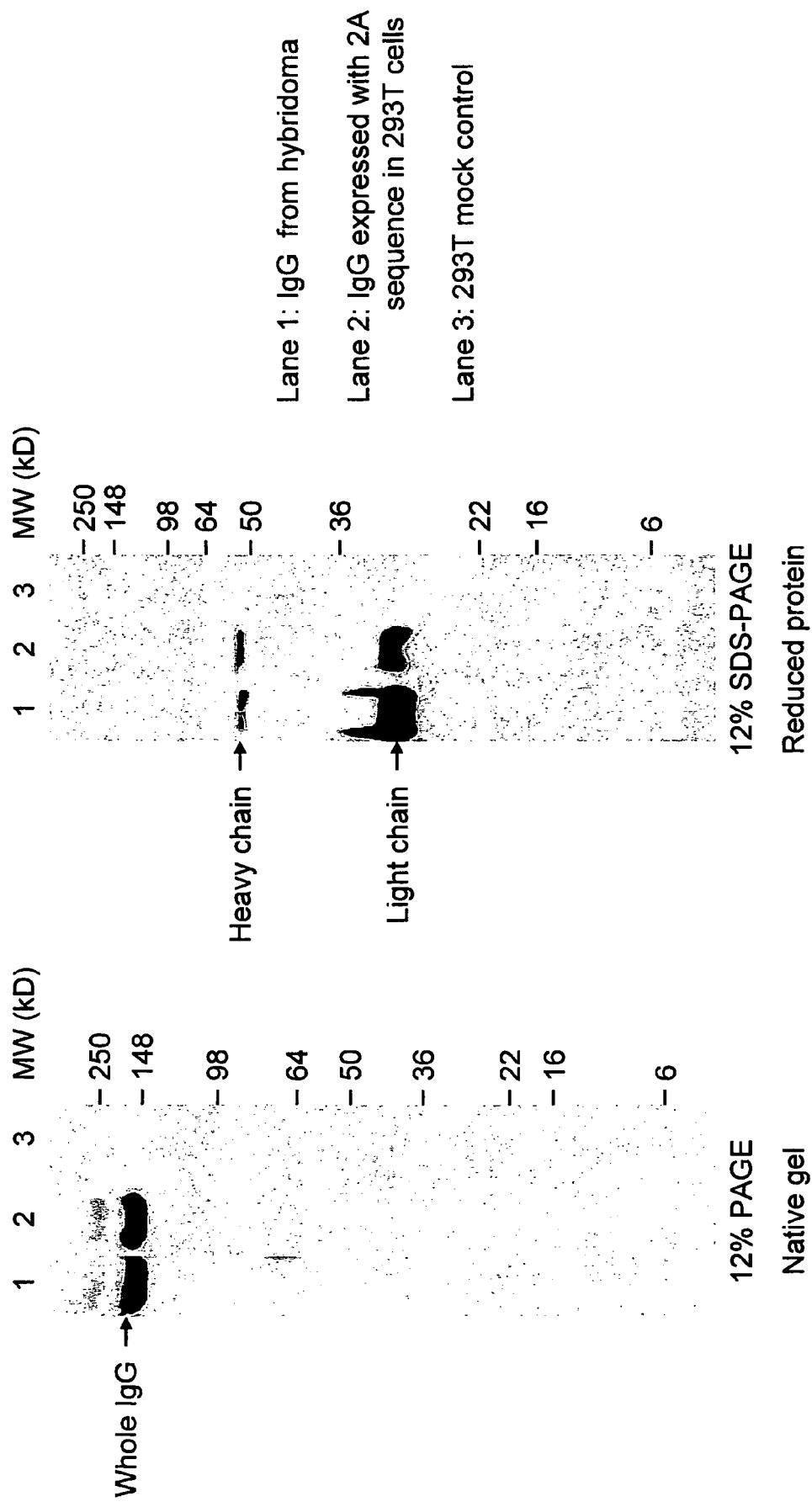
FIGS. 6A and B depict the protein characterization of IgG containing a 2A sequence in transfected 293T cells. The results from a Western blot analysis of IgG expressed by AAV H2AL construct under non-reducing (FIG. 6A) and reducing (FIG. 6B) conditions are shown.

Western blot analysis revealed that the antibodies from both the parental hybridoma cell line and the transfected 293T cells appear as an approximately 150 kD bands on a non-reducing gel. This indicates that the heavy and light chains generated via the 2A cleavage site dimerized properly with the heavy and light chain ratio demonstrating a 1:1 ratio, given that no additional bands, such as a 125 kD band which would indicate a heavy to light chain ratio of 2:1, were visible. On a reducing gel, the antibodies from both hybridoma and transfected 293T cells appeared as an approximately 50 kD band (heavy chain) and a 25 kD band (light chain). No uncleaved 75 kD precursor polyprotein was detected, indicating efficient cleavage by the 2A peptide (FIG. 6). Antibody expressed from the H2AL construct appeared slightly larger in molecular weight, presumably due to additional amino acid residues from the 2A sequence.

These results demonstrate that the 2A sequence provided a "cleavage" side facilitating the generation of both chains for the IgG molecule during the translation process of the molecule in the 293T cells. In other words, the chimeric H2AL polyprotein underwent autolytic cleavage to yield a full length, intact Ig having two heavy chains and two light chains following dimerization.

EXAMPLE 3

Expression of a Human IGG from an AAV H2AL Construct

In another example of the invention, the AAV 2A construct was used to express the heavy and light chain of a human monoclonal antibody to KDR. An AAV vector that encodes a novel human anti-VEGFR2 (KDR) mAb heavy chain, 2A, and light chain was constructed using the same strategy as described in Example 1. The AAV vector contains an EF1-alpha promoter, WPRE, and poly A sequence. 293T cells were transfected with the AAV plasmid by Fugen 6 kit as in Example 1 and cell supernatants were harvested 72 hours post-transfection. The concentrations of the mAb in 293T cell supernatants were determined using a sandwich ELISA assay from Bethyl Laboratories. In this assay, human IgG was captured by an immobilized anti-human IgG antibody on ELISA plates and detected by an anti-human IgG Fc antibody conjugated with HRP. Color was developed after adding substrate solution to the wells and mAb concentrations were calculated based on OD reading of the samples with the human IgG of known concentrations as a standard curve.

Figure 7:
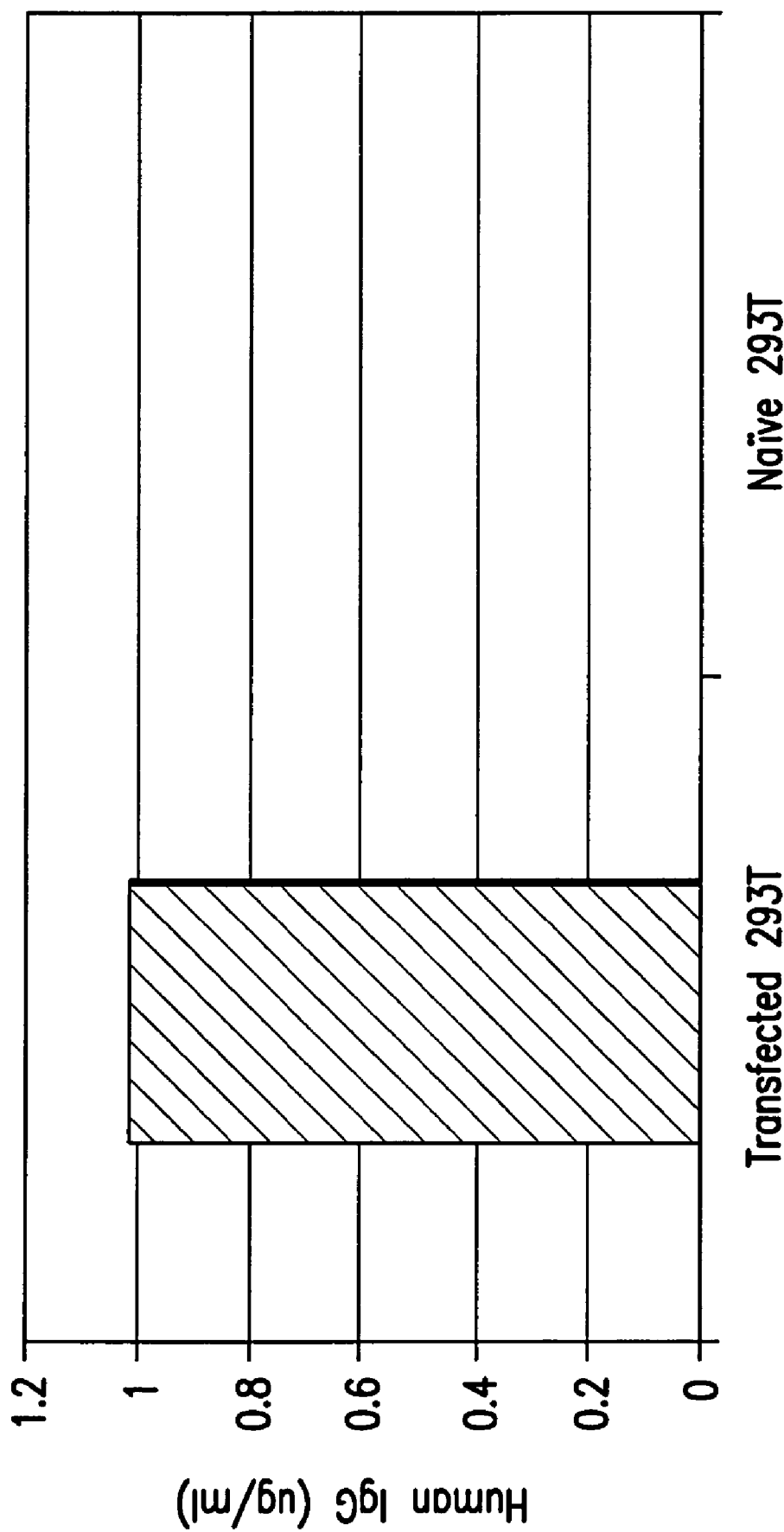
FIG. 7 demonstrates the expression of human anti-KDR monoclonal antibody in the supernatant of 293T cells transfected with anti-KDR Ig/AAV H2AL construct.

The results demonstrate that transfection of the AAV plasmid encoding the human antibody heavy and light chains linked by a 2A sequence into 293T cells resulted in high level of human antibody expression in cell culture supernatants (FIG. 7). Therefore, the antibody heavy and light chains can be generated from a single open reading frame through 2A sequence autocleavage. Furthermore, the heavy and light chains can be secreted properly from the transfected cells.

EXAMPLE 4

Expression of Rat Anti-FLK-1 MAB from an AAV H2AL Vector in Nude Mice via Plasmid Hydrodynamic Gene Transfer.

This experiment serves to demonstrate that high level antibody expression can be achieved in the serum of mice transduced with vector that encodes an rat anti-FLK-1 mAb heavy and light chain linked by the FMDV 2A sequence. The AAV vector was constructed as described in the Examples 1 and 2 and expression of the transgene was driven by an EF1-alpha promoter. The plasmid was purified with Qiagen's Mega plasmid DNA purification kit according to the manufacture's instructions. The plasmid DNA was dissolved in PBS in 25 ug/ml and injected into NCR nu/nu mice via tail veins by hydrodynamic gene transfer at a flow rate of 1 ml/10 g body weight within 10 seconds. Hydrodamic gene delivery is described in Zhang et al., Human Gene Ther., 10:1735-1737, 1999 and Liu et al., Gene Ther., 6:1258-1266, 1999. Orbital sinus blood was collected at day 3, 10 and 17.

Figure 8:
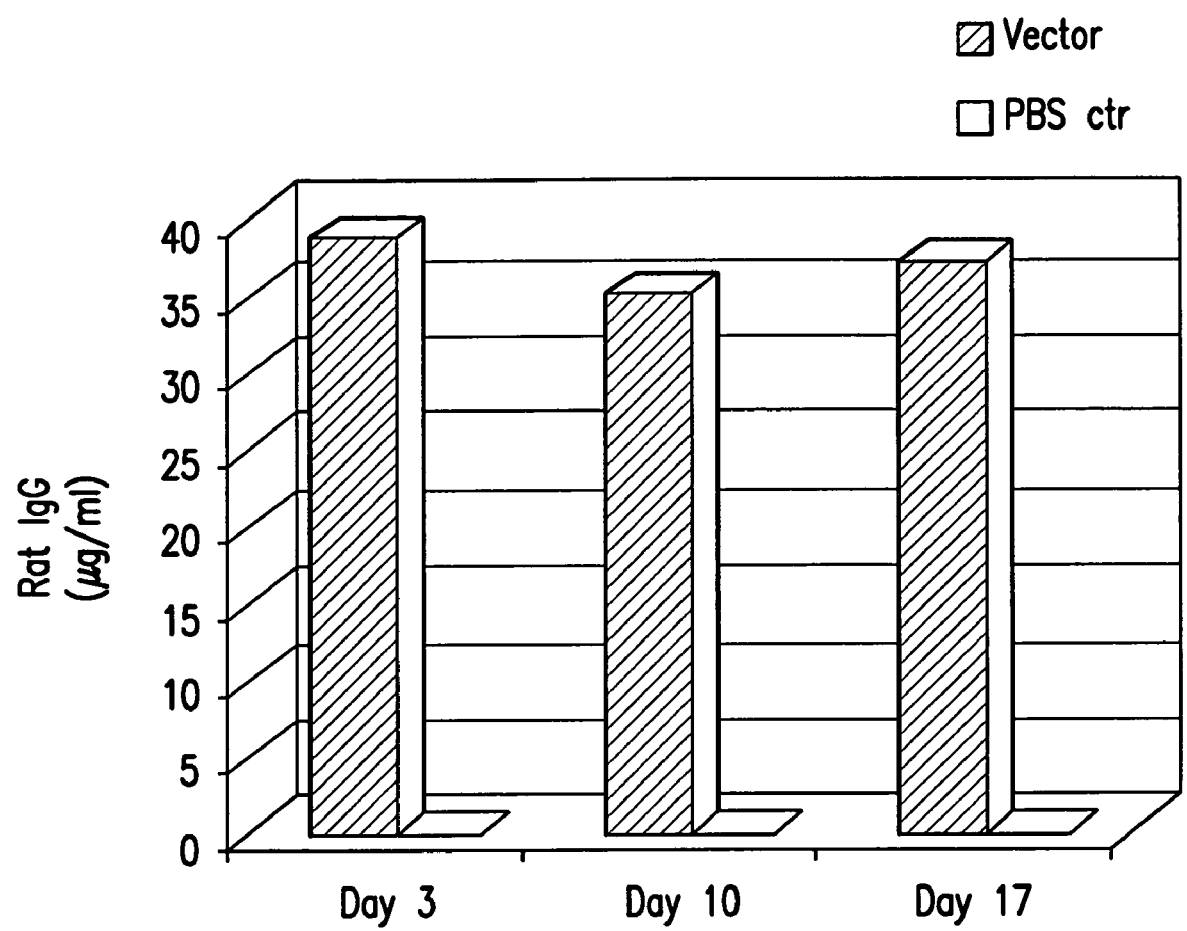
FIG. 8 demonstrates the expression of rat anti-FLK-1 IgG in mouse sera following in vivo gene transfer (hydrodynamic application) with an anti-FLK-1 Ig/AAV H2AL plasmid construct.

The sera from the mice injected with the plasmid DNA or a PBS control were analyzed for antibody concentrations using a rat IgG kit as described in Example 2. High level expression of the rat mAb was detected in mouse sera. In contrast, no rat antibody was present in the mouse injected with PBS only (FIG. 8).

Figure 9:
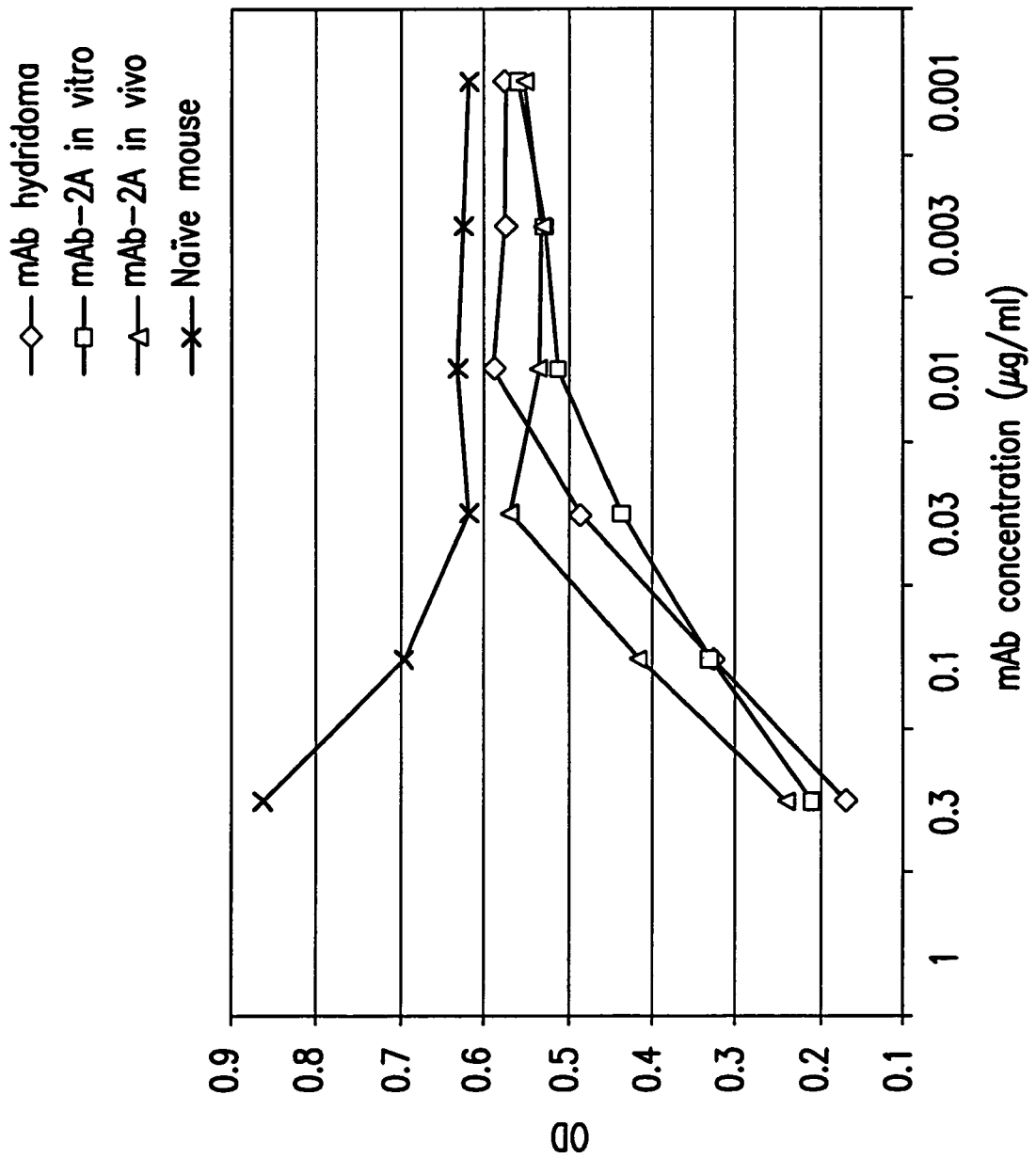
FIG. 9 demonstrates the biological activity of rat anti-FLK-1 IgG expressed in mouse sera following in vivo gene transfer (hydrodynamic application) with an anti-FLK-1 Ig/AAV H2AL plasmid construct.

Furthermore, it was shown that the antibody expressed in mouse serum retained biological activity, comparable to the parental antibody expressed from hybridoma cells, as determined by the neutralizing effect of the antibody in the VEGF-FLK-1 binding assay described in Example 2 (FIG. 9).

Figure 10:
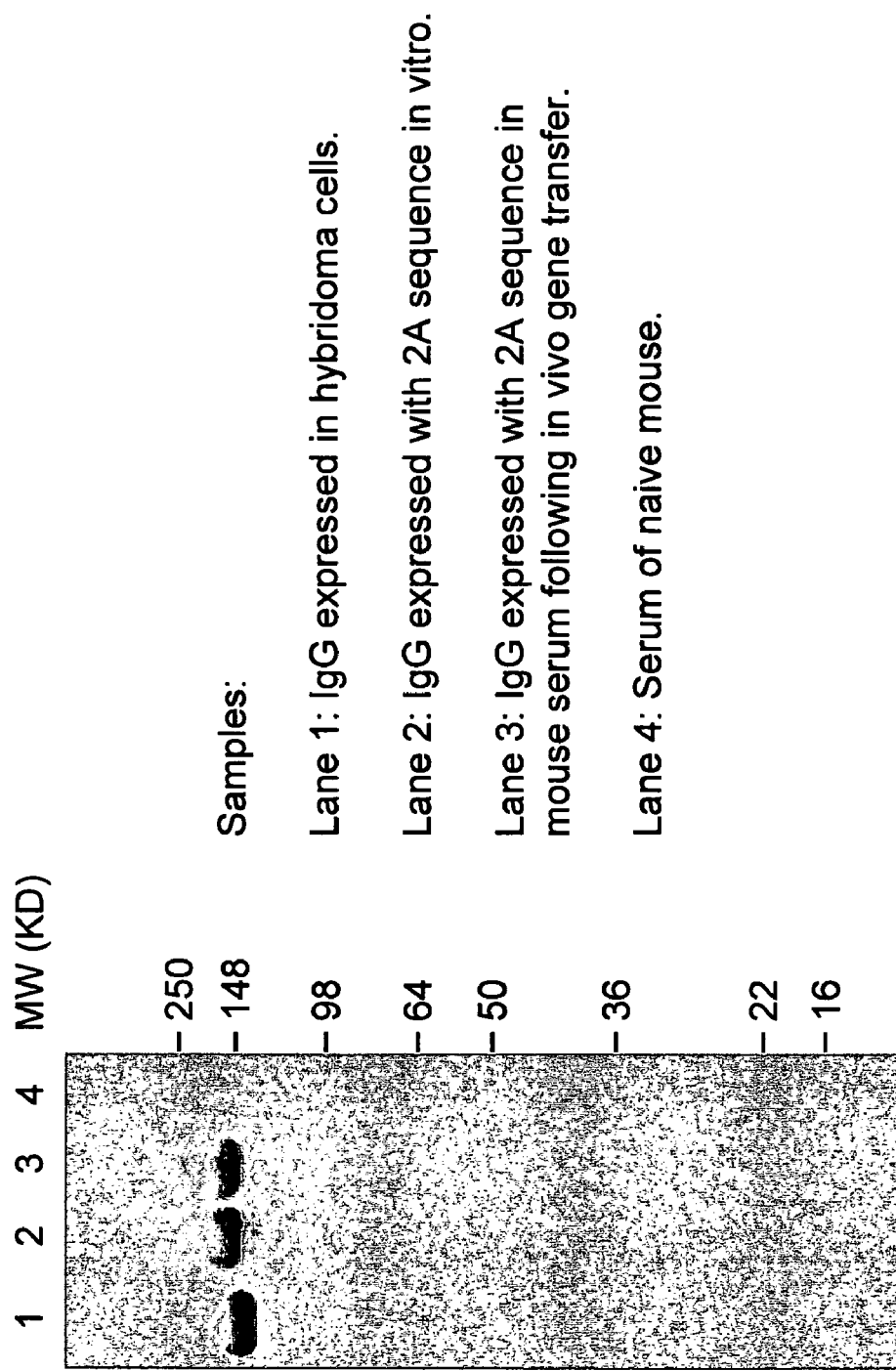
FIG. 10 depicts Western blot analysis of rat anti-FLK-1 immunoglobulin in mouse sera following in vivo gene transfer of the anti-FLK-1IgG/AAV H2AL construct.

To evaluate the cleavage efficiency of the 2A sequence and the molar ratio of the antibody heavy and light chains expressed in vivo, IgG from the mouse sera injected with or without vector was separated on a 12% Tris-Glycine gel under non-denaturing conditions, as described in Example 2. The separated proteins were transferred onto nitrocellular membranes using the Western blot procedure described in Example 2. As shown in FIG. 10, a protein band at approximately a 150 kD was observed in the serum of mice injected with the AAV H2AL vector, but not in the serum of control mice injected with PBS. This size is consistent with the expected molecular weight of the antibody in non-denatured condition, which is composed of two antibody heavy chains and two light chains following dimerization. This rat IgG band migrates at the same size as the antibody IgG expressed with the 2A sequence from the transiently transfected 293T cells and is slightly bigger than the IgG expressed from the parental hybridoma cells presumably due to additional amino acid residues derived from 2A sequence or posttranslational modifications.

Taken together, the results provided herein demonstrate that full-length functional antibodies can be expressed at high levels in vivo from an AAV vector driving a single open reading frame of an immunoglobulin heavy and light chain cDNA from a single promoter when provided with a 2A cleavage sequence between the two chains.

The 2A sequence facilitates efficient cleavage of the two peptides. The antibody heavy and light chains are properly folded and secreted, and form functional antibody with biological activity as potent as the original mAb from the hybridoma cells. The secreted antibody forms proper homodimers between two heavy chain peptides and heterodimers between a heavy and a light chain with an apparent 1:1 ratio as judged by a single band in a non-reducing protein gel.

Figure 11:
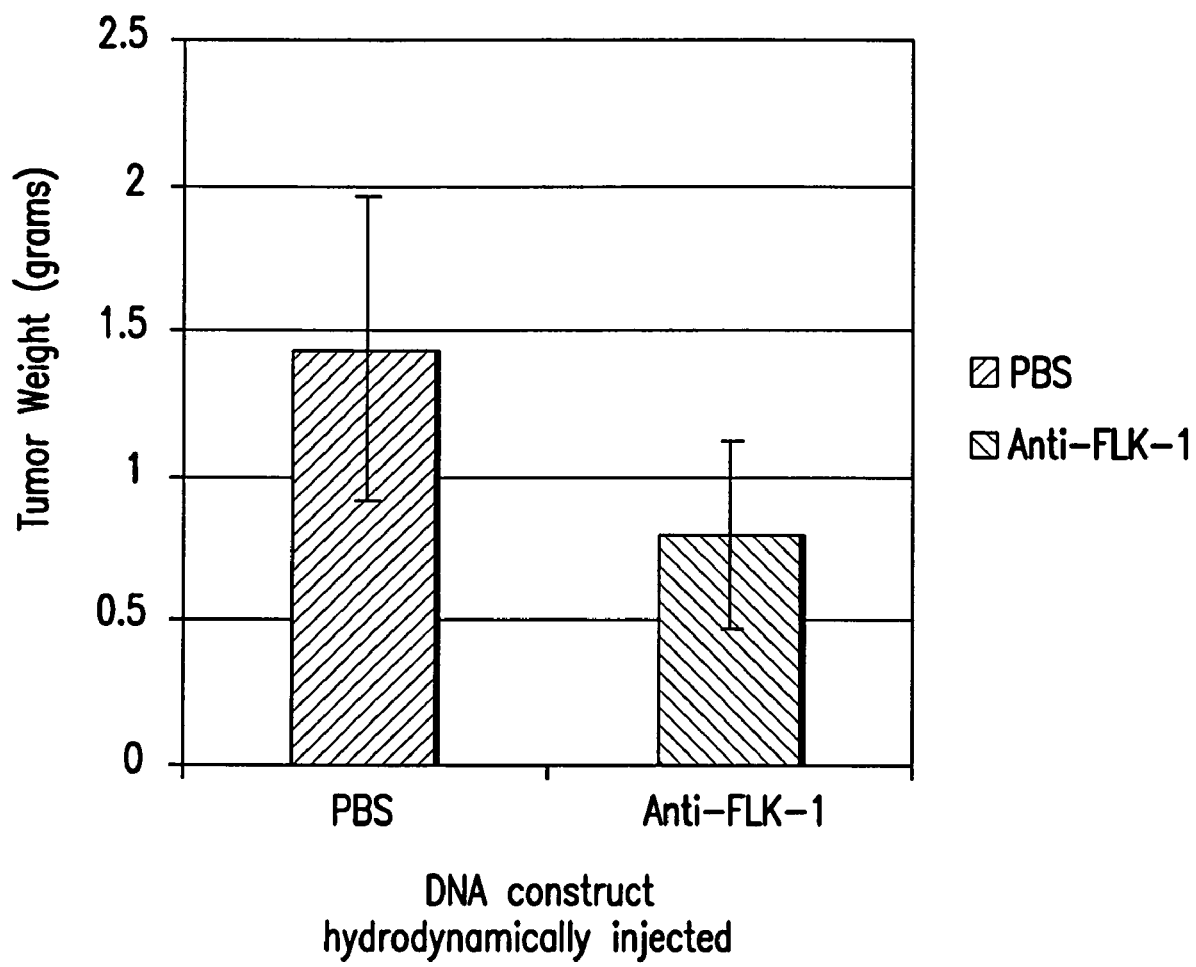
FIG. 11 depicts the results of an in vivo study wherein the weight of subcutaneous C6 glioma tumors was evaluated in animals following hydrodynamic delivery of an AAV EF1-alpha DC101 H2AL plasmid.

In vivo biological activity of the anti FLK-1 antibody was evaluated following hydrodynamic delivery of the AAV EF1-alpha DC101 H2AL plasmid in an NCR nu/nu animal model with subcutaneous C6 glioma tumors. Tumor weight was evaluated following hydrodynamic delivery of the anti-FLK-1 (anti KDR)-expressing plasmid and a reduction in tumor weight was evident in animals injected with the DC101 H2AL plasmid relative to untreated controls. The results are shown in FIG. 11.

What is claimed is:

1. An adeno-associated virus (AAV) vector for expression of a recombinant antibody or a recombinant antibody fragment having antigen-binding activity, wherein the antibody fragment is selected from the group consisting of Fab, F(ab')$_2$ and Fv(scFv) antibody fragments, the vector comprising in the 5' to 3' direction: a promoter operably linked to all of (1) a coding sequence for a heavy chain of the antibody or a fragment of the heavy chain, (2) a sequence encoding a furin proteolytic cleavage site, (3) a sequence encoding a 2A self-processing cleavage site and (4) a coding sequence for a light chain of the antibody or a fragment of the light chain.

2. The vector according to claim 1, wherein the 2A self-processing cleavage site is SEQ ID NO: 1.

3. The vector according to claim 1, wherein the coding sequence for the heavy chain of the antibody is the full length coding sequence.

4. The vector according to claim 1, wherein the coding sequence for the light chain of the antibody is the full length coding sequence.

5. The vector according to claim 1, wherein the 2A self-processing cleavage site is SEQ ID NO: 5.

6. The expression vector according to claim 5, wherein the promoter is selected from the group consisting of an elongation factor 1-alpha promoter (EF1α) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simiun virus 40 promoter (SV40) and a CK6 promoter.

7. The vector according to claim 6, wherein said promoter is the CAG promoter.

8. An isolated host cell transfected with the vector of claim 7.

9. An isolated host cell transfected with the vector of claim 5.

10. The vector according to claim 1, further comprising a signal sequence 5' to the coding sequence for the heavy chain of the antibody or the fragment of the heavy chain, or the coding sequence for the light chain of the antibody or the fragment of the light chain.

11. The vector according to claim 1, wherein the promoter is selected from the group consisting of an elongation factor 1-alpha promoter (EF1α) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

12. The vector according to claim 1, wherein the sequence encoding the furin cleavage site encodes an oligopeptide with the consensus sequence RXK(R)R (SEQ ID NO: 12).

13. An isolated host cell transfected with the vector of claim 12.

14. The vector according to claim 1, wherein the 2A self-processing cleavage site is SEQ ID NO: 8.

15. An adeno-associated virus (AAV) vector for the expression of a recombinant antibody or a recombinant antibody fragment having antigen-binding activity, wherein the recombinant antibody fragment is selected from the group consisting of Fab, F(ab')$_2$ and Fv(scFv) antibody fragments, the vector comprising in the 5' to 3' direction: a promoter operably linked to all of (1) a coding sequence for a heavy chain of the antibody or a fragment of the heavy chain, (2) a sequence encoding a furin cleavage site, (3) a sequence encoding a 2A self-processing cleavage site and (4) a coding sequence for a light chain of the antibody or a fragment of the light chain, wherein the 2A self-processing cleavage site is selected from the group consisting of the sequences presented as SEQ ID NO: 1, SEQ ID NO: 2, SEQ ID NO: 3, SEQ ID NO:4, SEQ ID NO: 5, SEQ ID NO: 6, SEQ ID NO: 7, and SEQ ID NO: 8, and wherein the heavy chain of the antibody or the fragment of the heavy chain and the light chain of the antibody or the fragment of the light chain are expressed in an equimolar ratio.

16. The vector according to claim 15, wherein the 2A self-processing cleavage site is SEQ ID NO: 1.

17. The vector according to claim 15, wherein the coding sequence of the heavy chain of the antibody is the full length coding sequence.

18. The vector according to claim 15, further comprising a signal sequence 5' to the coding sequence for the heavy chain of the antibody or the fragment of the heavy chain, or the coding sequence for the light chain of the antibody or the fragment of the light chain.

19. The vector according to claim 15, wherein the sequence encoding the furin cleavage site encodes an oligopeptide with the consensus sequence RXK(R)R (SEQ ID NO: 12).

20. An isolated host cell transfected with the vector of claim 19.

* * * * *

SEQUENCE LISTING

```
<160> NUMBER OF SEQ ID NOS: 12

<210> SEQ ID NO 1
<211> LENGTH: 19
<212> TYPE: PRT
<213> ORGANISM: Artificial Sequence
<220> FEATURE:
<223> OTHER INFORMATION: FMDV 2A domain polyprotein

<400> SEQUENCE: 1

Asn Phe Asp Leu Leu Lys Leu Ala Gly Asp Val Glu Ser Asn Pro Gly
 1               5                   10                  15

Pro Phe Phe

<210> SEQ ID NO 2
<211> LENGTH: 14
<212> TYPE: PRT
<213> ORGANISM: Artificial Sequence
<220> FEATURE:
<223> OTHER INFORMATION: variants of FMDV 2A domain polyprotein

<400> SEQUENCE: 2

Leu Leu Lys Leu Ala Gly Asp Val Glu Ser Asn Pro Gly Pro
 1               5                   10

<210> SEQ ID NO 3
<211> LENGTH: 17
<212> TYPE: PRT
<213> ORGANISM: Artificial Sequence
<220> FEATURE:
<223> OTHER INFORMATION: variants of FMDV 2A domain polyprotein

<400> SEQUENCE: 3

Asn Phe Asp Leu Leu Lys Leu Ala Gly Asp Val Glu Ser Asn Pro Gly
 1               5                   10                  15

Pro

<210> SEQ ID NO 4
<211> LENGTH: 20
<212> TYPE: PRT
<213> ORGANISM: Artificial Sequence
<220> FEATURE:
<223> OTHER INFORMATION: variants of FMDV 2A domain polyprotein

<400> SEQUENCE: 4

Gln Leu Leu Asn Phe Asp Leu Leu Lys Leu Ala Gly Asp Val Glu Ser
 1               5                   10                  15
```

-continued

```
Asn Pro Gly Pro
            20

<210> SEQ ID NO 5
<211> LENGTH: 24
<212> TYPE: PRT
<213> ORGANISM: Artificial Sequence
<220> FEATURE:
<223> OTHER INFORMATION: variants of FMDV 2A domain polyprotein

<400> SEQUENCE: 5

Ala Pro Val Lys Gln Thr Leu Asn Phe Asp Leu Leu Lys Leu Ala Gly
 1               5                  10                  15

Asp Val Glu Ser Asn Pro Gly Pro
            20

<210> SEQ ID NO 6
<211> LENGTH: 58
<212> TYPE: PRT
<213> ORGANISM: Artificial Sequence
<220> FEATURE:
<223> OTHER INFORMATION: variants of FMDV 2A domain polyprotein

<400> SEQUENCE: 6

Val Thr Glu Leu Leu Tyr Arg Met Lys Arg Ala Glu Thr Tyr Cys Pro
 1               5                  10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
        35                  40                  45

Ala Gly Asp Val Glu Ser Asn Pro Gly Pro
    50                  55

<210> SEQ ID NO 7
<211> LENGTH: 40
<212> TYPE: PRT
<213> ORGANISM: Artificial Sequence
<220> FEATURE:
<223> OTHER INFORMATION: variants of FMDV 2A domain polyprotein

<400> SEQUENCE: 7

Leu Leu Ala Ile His Pro Thr Glu Ala Arg His Lys Gln Lys Ile Val
 1               5                  10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 8
<211> LENGTH: 33
<212> TYPE: PRT
<213> ORGANISM: Artificial Sequence
<220> FEATURE:
<223> OTHER INFORMATION: variants of FMDV 2A domain polyprotein

<400> SEQUENCE: 8

Glu Ala Arg His Lys Gln Lys Ile Val Ala Pro Val Lys Gln Thr Leu
 1               5                  10                  15

Asn Phe Asp Leu Leu Lys Leu Ala Gly Asp Val Glu Ser Asn Pro Gly
            20                  25                  30

Pro
```

```
<210> SEQ ID NO 9
<211> LENGTH: 5
<212> TYPE: PRT
<213> ORGANISM: Artificial Sequence
<220> FEATURE:
<223> OTHER INFORMATION: proteolytic cleavage sites

<400> SEQUENCE: 9

Ile Glu Asp Gly Arg
 1               5

<210> SEQ ID NO 10
<211> LENGTH: 6
<212> TYPE: PRT
<213> ORGANISM: Artificial Sequence
<220> FEATURE:
<223> OTHER INFORMATION: proteolytic cleavage sites

<400> SEQUENCE: 10

Leu Val Pro Arg Gly Ser
 1               5

<210> SEQ ID NO 11
<211> LENGTH: 10
<212> TYPE: PRT
<213> ORGANISM: Artificial Sequence
<220> FEATURE:
<223> OTHER INFORMATION: proteolytic cleavage sites

<400> SEQUENCE: 11

Leu Ala Gly Phe Ala Thr Val Ala Gln Ala
 1               5                  10

<210> SEQ ID NO 12
<211> LENGTH: 5
<212> TYPE: PRT
<213> ORGANISM: Artificial Sequence
<220> FEATURE:
<223> OTHER INFORMATION: proteolytic cleavage sites
<220> FEATURE:
<221> NAME/KEY: VARIANT
<222> LOCATION: 2
<223> OTHER INFORMATION: Xaa = Any Amino Acid

<400> SEQUENCE: 12

Arg Xaa Lys Arg Arg
 1               5
```